US012201518B2

(12) United States Patent
Matheny

(10) Patent No.: US 12,201,518 B2
(45) Date of Patent: Jan. 21, 2025

(54) REINFORCED PROSTHETIC VALVES

(71) Applicant: CorMatrix Cardiovascular, Inc., Roswell, GA (US)

(72) Inventor: Robert G Matheny, Norcross, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 897 days.

(21) Appl. No.: 17/178,562

(22) Filed: Feb. 18, 2021

(65) Prior Publication Data

US 2021/0169647 A1 Jun. 10, 2021

Related U.S. Application Data

(63) Continuation-in-part of application No. 16/440,504, filed on Jun. 13, 2019, now Pat. No. 11,160,903, and
(Continued)

(51) Int. Cl.
*A61F 2/24* (2006.01)
*A61L 27/04* (2006.01)
(Continued)

(52) U.S. Cl.
CPC .......... *A61F 2/2418* (2013.01); *A61F 2/2457* (2013.01); *A61L 27/042* (2013.01);
(Continued)

(58) Field of Classification Search
CPC ............ A61F 2/2418; A61F 2210/0014; A61F 2230/0067; A61F 2/2457; A61L 27/16;
(Continued)

(56) References Cited

U.S. PATENT DOCUMENTS 6,117,979 A  9/2000 Hendriks et al.
2013/0190860 A1  7/2013 Sundt
(Continued)

FOREIGN PATENT DOCUMENTS

WO  2014/133539 A1  9/2014
WO  2016/050751 A1  4/2016

OTHER PUBLICATIONS

Extended Search Report, EP Application No. 24153745.5, mailed Apr. 16, 2024.
(Continued)

*Primary Examiner* — Suba Ganesan
(74) *Attorney, Agent, or Firm* — Thomas | Horstemeyer, LLP

(57) ABSTRACT

A prosthetic valve comprising a conical shaped sheet structure and a support structure, the sheet structure having a closed distal end and a plurality of elongated ribbon members that are positioned proximate each other in a joined relationship, whereby the ribbon members form a plurality of fluid flow modulating regions that close when fluid flow through the valve exhibits a negative flow pressure and open when fluid flow through the valve exhibits a positive flow pressure, the support structure having at least one elongated cardiovascular structure engagement member that is associated with one of the ribbon members and adapted to engage a cardiovascular structure.

23 Claims, 17 Drawing Sheets

Related U.S. Application Data a continuation-in-part of application No. 16/129,968, filed on Sep. 13, 2018, now Pat. No. 10,952,843, and a continuation-in-part of application No. 15/206,833, filed on Jul. 11, 2016, now Pat. No. 10,188,510, and a continuation-in-part of application No. 14/960,354, filed on Dec. 5, 2015, now Pat. No. 9,907,649, and a continuation-in-part of application No. 14/229,854, filed on Mar. 29, 2014, now Pat. No. 9,308,084.

(51) Int. Cl.
| | | |
|---|---|---|
| *A61L 27/06* | (2006.01) | |
| *A61L 27/16* | (2006.01) | |
| *A61L 27/18* | (2006.01) | |
| *A61L 27/22* | (2006.01) | |
| *A61L 27/24* | (2006.01) | |
| *A61L 27/34* | (2006.01) | |
| *A61L 27/36* | (2006.01) | |
| *A61L 27/38* | (2006.01) | |
| *A61L 27/54* | (2006.01) | |

(52) U.S. Cl.
CPC ............ *A61L 27/047* (2013.01); *A61L 27/06* (2013.01); *A61L 27/16* (2013.01); *A61L 27/18* (2013.01); *A61L 27/225* (2013.01); *A61L 27/227* (2013.01); *A61L 27/24* (2013.01); *A61L 27/34* (2013.01); *A61L 27/3625* (2013.01); *A61L 27/3633* (2013.01); *A61L 27/367* (2013.01); *A61L 27/3826* (2013.01); *A61L 27/3834* (2013.01); *A61L 27/3873* (2013.01); *A61L 27/54* (2013.01); *A61F 2210/0014* (2013.01); *A61F 2230/0067* (2013.01); *A61L 2300/402* (2013.01); *A61L 2300/406* (2013.01); *A61L 2300/408* (2013.01); *A61L 2300/41* (2013.01); *A61L 2300/414* (2013.01); *A61L 2300/416* (2013.01); *A61L 2300/42* (2013.01)

(58) Field of Classification Search
CPC .......... A61L 27/18; A61L 27/24; A61L 27/34; A61L 27/54; A61L 2300/414
See application file for complete search history.

(56) References Cited

U.S. PATENT DOCUMENTS

| | | |
|---|---|---|
| 2014/0005773 A1 | 1/2014 | Wheatly |
| 2014/0067048 A1 | 3/2014 | Chau et al. |
| 2014/0330369 A1 | 11/2014 | Matheny |
| 2016/0317300 A1* | 11/2016 | Matheny ................ A61L 27/50 |
| 2018/0153686 A1 | 6/2018 | Matheny |
| 2019/0008634 A1 | 1/2019 | Matheny |
| 2019/0358034 A1 | 11/2019 | Tabata |
| 2020/0022808 A1 | 1/2020 | Matheny |
| 2020/0069840 A1 | 3/2020 | Matheny |
| 2020/0368178 A1 | 11/2020 | Naso et al. |

OTHER PUBLICATIONS

Extended European Search Report for EP Application No. 21926991.7 mailed Oct. 16, 2024.
Extended European Search Report for EP Application No. 21926982.6 mailed Oct. 16, 2024.
Extended European Search Report for EP Application No. 21926977.6 mailed Oct. 17, 2024.

* cited by examiner

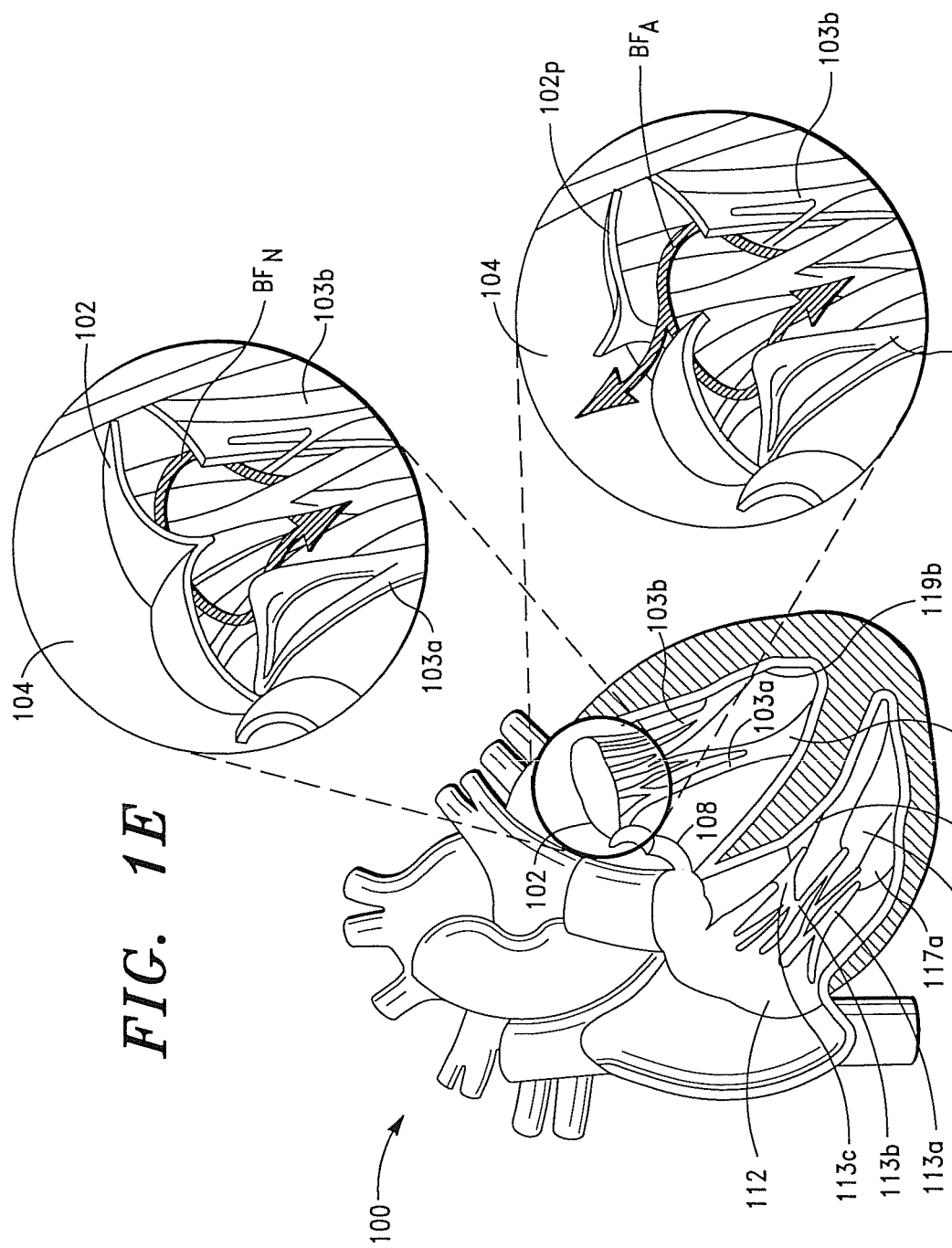

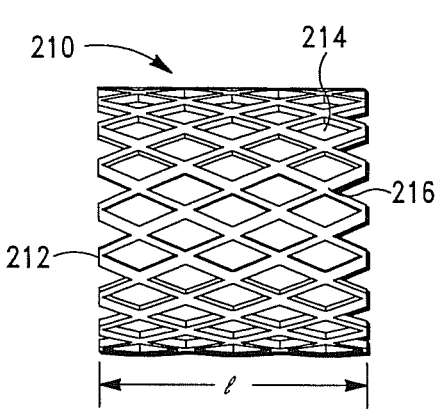
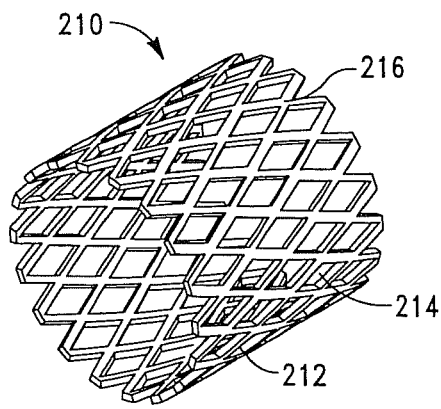
FIG. 4A                FIG. 4B
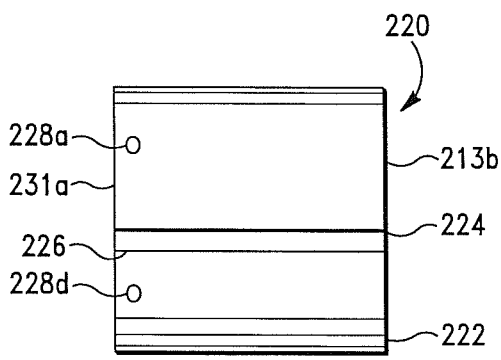
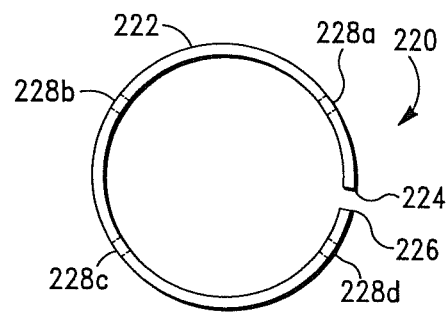
FIG. 5A                FIG. 5B
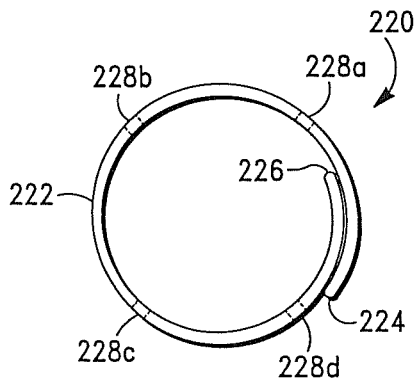
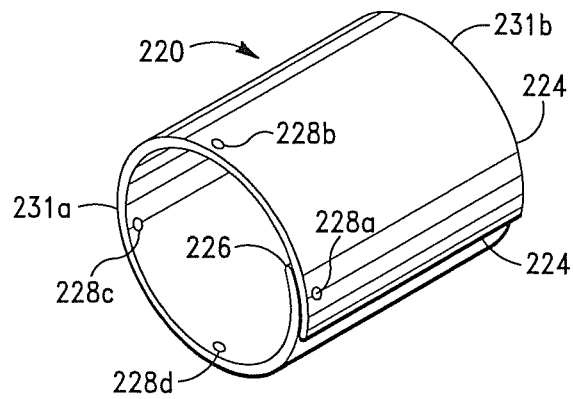
FIG. 6A                FIG. 6B

REINFORCED PROSTHETIC VALVES

CROSS-REFERENCE TO RELATED APPLICATIONS

This application is a continuation-in-part of U.S. application Ser. No. 16/440,504, filed Jun. 13, 2019, which is a continuation-in-part of U.S. application Ser. No. 16/129,968, filed on Sep. 13, 2018, which is a continuation-in-part of U.S. application Ser. No. 15/206,833, filed on Jul. 11, 2016, now U.S. Pat. No. 10,188,510, which is a continuation-in-part application of U.S. application Ser. No. 14/960,354, filed on Dec. 5, 2015, now U.S. Pat. No. 9,907,649, which is a continuation-in-part application of U.S. application Ser. No. 14/229,854, filed on Mar. 29, 2014, now U.S. Pat. No. 9,308,084.

FIELD OF THE INVENTION

The present invention generally relates to prosthetic valves for replacing defective heart valves. More particularly, the present invention relates to prosthetic heart valves and methods for anchoring same to cardiovascular structures and/or tissue.

BACKGROUND OF THE INVENTION

As is well known in the art, the human heart has four valves that control blood flow circulating through the human body. Referring to FIGS. 1A and 1B, on the left side of the heart 100 is the mitral valve 102, located between the left atrium 104 and the left ventricle 106, and the aortic valve 108, located between the left ventricle 106 and the aorta 110. Both of these valves direct oxygenated blood from the lungs into the aorta 110 for distribution through the body.

The tricuspid valve 112, located between the right atrium 114 and the right ventricle 116, and the pulmonary valve 118, located between the right ventricle 116 and the pulmonary artery 120, however, are situated on the right side of the heart 100 and direct deoxygenated blood from the body to the lungs.

Referring now to FIGS. 1C and 1D, there are also generally five papillary muscles in the heart 100; three in the right ventricle 116 and two in the left ventricle 106. The anterior, posterior and septal papillary muscles 117a, 117b, 117c of the right ventricle 116 each attach via chordae tendineae 113a, 113b, 113c to the tricuspid valve 112. The anterior and posterior papillary muscles 119a, 119b of the left ventricle 106 attach via chordae tendineae 103a, 103b to the mitral valve 102 (see also FIG. 1E).

Since heart valves are passive structures that simply open and close in response to differential pressures, the issues that can develop with valves are typically classified into two categories: (i) stenosis, in which a valve does not open properly, and (ii) insufficiency (also called regurgitation), in which a valve does not close properly.

Stenosis and insufficiency can occur as a result of several abnormalities, including damage or severance of one or more chordae or several disease states. Stenosis and insufficiency can also occur concomitantly in the same valve or in different valves.

Both of the noted valve abnormalities can adversely affect organ function and result in heart failure. By way of example, referring first to FIG. 1E, there is shown normal blood flow (denoted "$BF_N$") proximate the mitral valve 102 during closure. Referring now to FIG. 1F, there is shown abnormal blood flow (denoted "$BF_A$") or regurgitation caused by a prolapsed mitral valve 102p. As illustrated in FIG. 1F, the regurgitated blood "$BF_A$" flows back into the left atrium, which can, if severe, result in heart failure.

In addition to stenosis and insufficiency of a heart valve, surgical intervention may also be required for certain types of bacterial or fungal infections, wherein the valve may continue to function normally, but nevertheless harbors an overgrowth of bacteria (i.e., "vegetation") on the valve leaflets. The vegetation can, and in many instances will, flake off (i.e., "embolize") and lodge downstream in a vital artery.

If such vegetation is present on the valves of the left side (i.e., the systemic circulation side) of the heart, embolization can, and often will, result in sudden loss of the blood supply to the affected body organ and immediate malfunction of that organ. The organ most commonly affected by such embolization is the brain, in which case the patient can, and in many instances will, suffer a stroke.

Likewise, bacterial or fungal vegetation on the tricuspid valve can embolize to the lungs. The noted embolization can, and in many instances will, result in lung dysfunction.

Treatment of the noted heart valve dysfunctions typically comprises reparation of the diseased heart valve with preservation of the patient's own heart valve or replacement of the valve with a mechanical or bioprosthetic heart valve, i.e., a prosthetic heart valve.

Various prosthetic heart valves have thus been developed for replacement of native diseased or defective heart valves. The selection of a particular type of prosthetic heart valve depends on many factors, such as the location of the diseased or defective native valve, the age and other specifics of the recipient of the replacement heart valve, and the surgeon's experiences and preferences.

Commonly used prosthetic heart valve are typically classified in the following three groups: (i) mechanical valves, (ii) allograft tissue valves, and (iii) xenograft tissue valves. Each of the noted valves and disadvantages associated with same are discussed in detail below.

Mechanical Heart Valves

As is well known in the art, mechanical heart valves, such as caged-ball valves, bi-leaflet valves, and tilting disk valves, typically comprise various metal and polymeric components, which can, and in most instances will, induce an adverse inflammatory response when implanted in a patient or subject.

A further disadvantage associated with mechanical heart valves is that such valves also have a propensity to cause the formation of blood clots after implantation in a patient. If such blood clots form on the mechanical valve, they can preclude the valve from opening or closing correctly or, more importantly, can disengage from the valve and embolize to the brain, causing an embolic stroke. Thus, recipients of a mechanical heart valve are typically required to take systemic anticoagulant drugs for the rest of their lives. In addition to being expensive, these anticoagulant drugs can themselves be dangerous in that they can cause abnormal bleeding in the recipient or patient that can lead to a hemorrhagic stroke.

A further disadvantage associated with mechanical heart valves is that such valves often have large and cumbersome skirt attachments that partially extend into the left atrium and the left ventricle when implanted in a mitral valve region. The skirt attachment can, and often will, impair aortic valve function by obstructing the outflow tract of the aortic valve and preventing the leaflets of the adjacent aortic valve from coapting. In some instances, mechanical heart valves can reduce the outflow blood rate of the aortic valve by up to 50%.

The risks and complications associated with impaired aortic valve function typically include left ventricular hypertrophy with fibrosis, systolic dysfunction (a decrease in the ejection fraction), diastolic dysfunction (elevated filling pressure of the LV), and in severe cases, congestive heart failure.

Further, mechanical heart valves with and without the skirt attachments are notoriously difficult to implant and often require large and cumbersome catheter assemblies for percutaneous or transapical implantation. These large catheter assemblies are excessively difficult to operate during a percutaneous or transapical implantation procedure.

Allograft Tissue Valves

As is also well known in the art, allograft tissue valves are harvested from human sources, such as human cadavers. Unlike mechanical heart valves, allograft tissue valves typically do not promote blood clot formation and, therefore, avoid the need for prescribing an anticoagulant medication for the recipient or patient. However, there are still several drawbacks and disadvantages associated with allograft tissue valves.

A major drawback associated with allograft tissue valves is that such valves are not available in sufficient numbers to satisfy the needs of all patients who need new heart valves.

A further major drawback associated with allograft tissue valves is that recipients of allograft tissue valves, i.e., patients, are typically required to take systemic antirejection and/or immunosuppressive drugs for a predetermined period of time and, in some instances, for a lifetime. Although antirejection and/or immunosuppressive drugs increase the possibility that a patient will accept an allograft without complications, the drugs will often leave the recipient vulnerable to a plurality of other infectious diseases, including bacterial infections, fungal infections, viral infections and the like.

Xenograft Tissue Valves

As is additionally well known in the art, xenograft tissue valves are formed from non-human tissue sources, such as cows or pigs. Xenograft tissue valves are similarly less likely to cause blood clot formation than comparable mechanical valves. However, there are also several drawbacks and disadvantages associated with most conventional allograft tissue valves.

A major drawback associated with conventional xenograft tissue valves is that such valves often comprise glutaraldehyde processed tissue and, hence, are prone to calcification and lack the long-term durability of mechanical valves.

More recently, remodelable xenograft tissue valves comprising decellularized extracellular matrix (ECM) have been developed and employed to replace native diseased or defective heart valves. Such valves are not prone to calcification and, as set forth in Applicant's U.S. Pat. Nos. 9,308,084, 9,011,526, 8,709,076 and Co-pending U.S. application Ser. No. 16/129,968, which are expressly incorporated by reference herein in their entirety, have the capacity to remodel, i.e., form valve structures similar to native valve structures when implanted in a patient, and induce remodeling of native cardiovascular tissue and regeneration of new cardiovascular tissue when implanted in a patient.

Although most remodelable xenograft ECM tissue valves substantially reduce and, in most instances, eliminate the major disadvantages and drawbacks associated with mechanical valves, allograft tissue valves, and conventional xenograft tissue valves, a remaining drawback associated with mechanical valves, allograft tissue valves, and xenograft tissue valves (non-remodelable and remodelable) is obtaining a secure and reliable engagement of the noted prosthetic heart valves to cardiovascular structures; the most common structures being the valve annulus and papillary muscles.

Various apparatus and surgical methods have thus been developed for obtaining a secure and reliable engagement of prosthetic heart valves to cardiovascular structures.

The most common surgical method that is employed to engage a prosthetic heart valve; particularly, a prosthetic heart valve comprising mammalian tissue, to a valve annulus comprises employing an annular ring, e.g., a circular synthetic ring, which, in some instances is disposed on the proximal end of the valve, such as described and illustrated in Applicant's U.S. Pat. Nos. 9,044,319, 10,188,509, 10,188,510 and 10,052,409, and suturing the annular ring and associated valve directly to the valve annulus.

The most common surgical method that is employed to engage a prosthetic heart valve, and again, particularly, a prosthetic heart valve comprising mammalian tissue, to papillary muscles is to suture the distal end(s) of the prosthetic heart valve directly to one or more papillary muscles.

As is well known in the art, there are several significant drawbacks and disadvantages associated with securing prosthetic heart valves directly to papillary muscles.

A major drawback associated with securing prosthetic heart valves directly to papillary muscles is that doing so can, and in many instances will, adversely impact the structural integrity and, thereby, function of the prosthetic heart valve.

A further drawback is that such engagement results in a very high stress region during cardiac cycles, which often results in a rupture of the valve and/or muscle and, thereby catastrophic failure of the valve.

There thus remains a need for improved prosthetic valves that can readily and reliably be secured to cardiovascular structures and maintain structural integrity during cardiac cycles.

There also remains a need for improved methods of securely and reliably securing prosthetic heart valves; particularly, prosthetic heart valves comprising mammalian tissue, to cardiovascular structures and/or tissue.

It is therefore an object of the present invention to provide improved prosthetic valves that can readily and reliably be secured to cardiovascular structures and maintain structural integrity during cardiac cycles.

It is another object of the present invention to provide apparatus, systems and methods for attaching prosthetic heart valves to cardiovascular structures and/or tissue that achieve secure and reliable engagement of the prosthetic heart valves to the cardiovascular structures and/or tissue and preserve the structural integrity of the prosthetic heart valves and cardiovascular structure(s) when attached thereto.

It is another object of the present invention to provide improved prosthetic heart valves with minimal in vivo calcification and cytotoxicity.

It is another object of the present invention to provide prosthetic heart valves having the capacity to deliver biologically active agents, such as growth factors, and pharmacological agents, such as anti-inflammatories, to cardiovascular tissue, when disposed proximate thereto.

SUMMARY OF THE INVENTION

The present invention is directed to prosthetic heart valves that can be readily employed to selectively replace diseased or defective heart valves, and methods for attaching (or anchoring) same to cardiovascular structures and/or tissue.

In some embodiments of the invention, the prosthetic valves comprise continuous conical shaped structures.

In some embodiments, the conical shaped structures comprise sheet members or structures.

In some embodiments of the invention, the sheet members comprise ribbon structures.

In some embodiments, the sheet members comprise seamless ribbon structures that are formed from pre-formed sheet structures.

According to the invention, the sheet members and, thereby, prosthetic valves formed therewith comprise a single sheet structure or multiple sheet structures, e.g., two sheet structures, three sheet structures, etc.

In a preferred embodiment, the sheet members and, thereby, prosthetic valves formed therewith comprise a plurality of elongated ribbon members.

In a preferred embodiment, the sheet members and, thereby, prosthetic valves formed therewith comprise a plurality of fluid flow modulating regions.

In some embodiments of the invention, the prosthetic valves comprise mammalian-based tissue.

In some embodiments, the mammalian-based tissue comprises an ECM composition comprising acellular ECM derived from a mammalian tissue source.

In some embodiments, the mammalian-based tissue comprises collagenous mammalian tissue derived from a mammalian tissue source.

In some embodiments of the invention, the collagenous mammalian tissue comprises pericardium tissue.

In some embodiments of the invention, the prosthetic valves comprise a polymeric composition comprising at least one biocompatible polymer.

In some embodiments of the invention, the biocompatible polymer comprises polyurethane urea (Artelon®), poly(ε-caprolactone) (PCL), polyethylene terephthalate (Dacron™) or polytetrafluoroethylene (PTFE).

In some embodiments of the invention, the mammalian-based tissue and/or polymeric composition (and, hence, prosthetic valves formed therefrom) further comprises at least one additional biologically active agent or composition, i.e., an agent or composition that induces or modulates a physiological or biological process, or cellular activity, e.g., induces proliferation, and/or growth and/or regeneration of tissue.

In some embodiments of the invention, the biologically active agent comprises a growth factor, including, without limitation, transforming growth factor beta (TGF-β), fibroblast growth factor-2 (FGF-2), and vascular endothelial growth factor (VEGF).

In some embodiments of the invention, the mammalian-based tissue and/or polymeric composition (and, hence, prosthetic valves formed therefrom) further comprises at least one pharmacological agent or composition (or drug), i.e., an agent or composition that is capable of producing a desired biological effect in vivo, e.g., stimulation or suppression of apoptosis, stimulation or suppression of an immune response, etc.

Suitable pharmacological agents and compositions include, without limitation, antibiotics, anti-fibrotics, antiviral agents, analgesics, anti-inflammatories, anti-neoplastics, anti-spasmodics, and anti-coagulants and/or anti-thrombotic agents.

In a preferred embodiment of the invention, the prosthetic valves comprise a support structure that facilitates engagement of the valves to cardiovascular tissue and associated cardiovascular structures.

In some embodiments, the support structure is further designed and configured to (i) reinforce the prosthetic valves and (ii) position the valves proximate a cardiovascular structure, e.g., valve annulus (and, hence, cardiovascular tissue associated therewith) and maintain contact therewith for a pre-determined period of time.

According to the invention, the support structure can comprise various biocompatible materials.

In some embodiments of the invention, the support structure thus comprises a biocompatible metal.

According to the invention, suitable biocompatible metals include, without limitation, Nitinol®, stainless steel and titanium.

In some embodiments, the support structure comprises a polymeric composition comprising at least one biocompatible polymer.

According to the invention, suitable biocompatible polymers similarly include, without limitation, polyurethane urea (Artelon®), poly(ε-caprolactone) (PCL), and poly (glycerol sebacate) (PGS).

In a preferred embodiment of the invention, the support structure comprises Dyneema®, a high strength, ultra-high molecular weight polyethylene (UHMwPE).

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 1A-1D are schematic illustrations of a human heart;

FIG. 1E is an illustration of a normal mitral valve;

FIG. 1F is an illustration of a prolapsed mitral valve;

FIG. 4A is a front plan view of one embodiment of a support structure annular ring, in accordance with the invention;

FIG. 4B is a perspective view of the annular ring shown in FIG. 4A, in accordance with the invention;

FIG. 5A is a front plan view of another embodiment of support structure annular ring, in accordance with the invention;

FIG. 5B is a perspective view of the annular ring member shown in FIG. 5A, in accordance with the invention;

FIG. 6A is a side view of the annular ring shown in FIG. 5A in a pre-deployment configuration, in accordance with the invention;

FIG. 6B is a perspective view of the annular ring shown in FIG. 6A, in accordance with the invention;

DETAILED DESCRIPTION OF THE PREFERRED EMBODIMENT

Figure 1A:
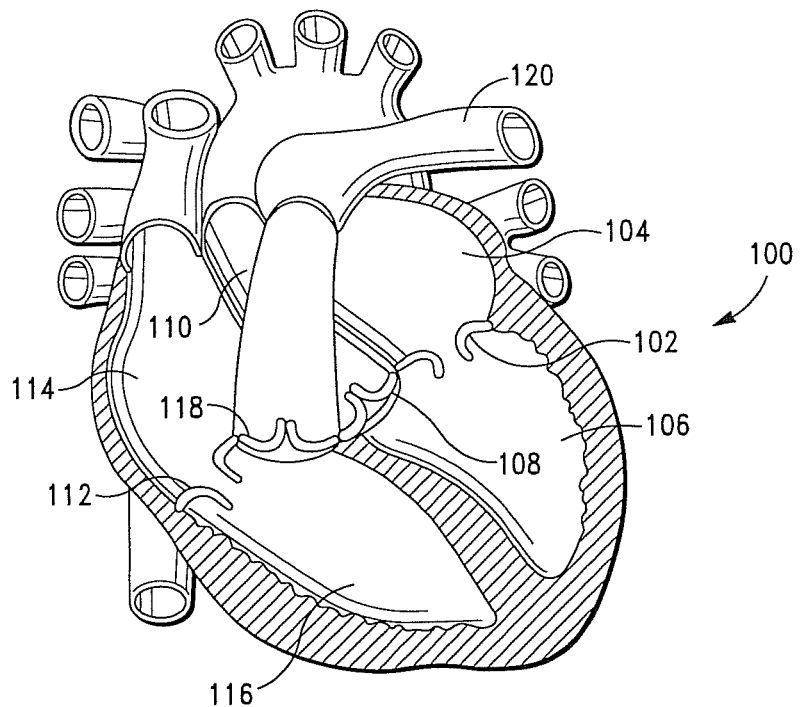
Figure 1B:
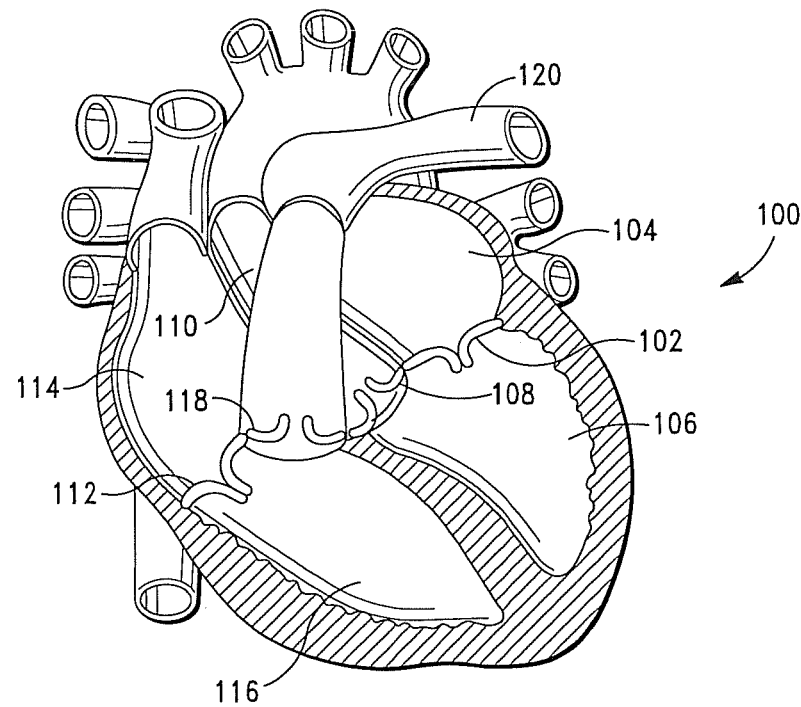
Figure 1C:
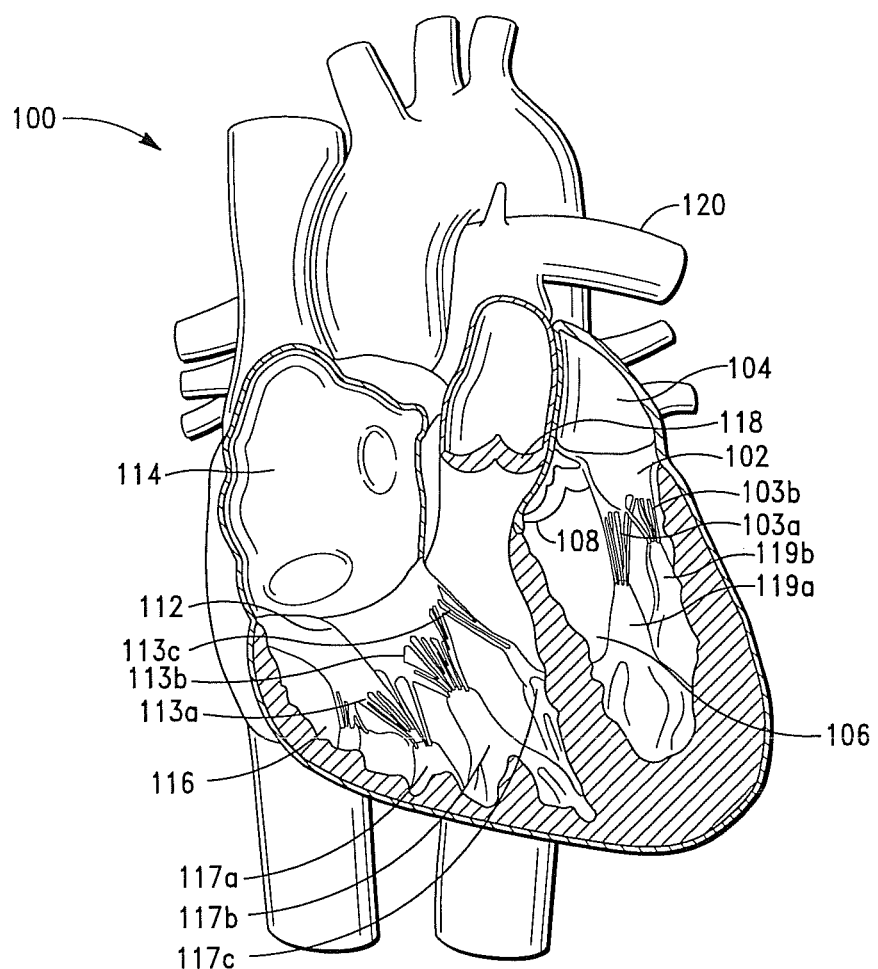

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein are hereby incorporated by reference herein in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "extracellular matrix", "ECM", and "ECM material" are used interchangeably herein, and mean and include a collagen-rich substance that is found in between cells in mammalian tissue, and any material processed therefrom, e.g., decellularized ECM.

The term "acellular ECM", as used herein, means ECM that has a reduced content of cells.

According to the invention, ECM can be derived from a variety of mammalian tissue sources and tissue derived therefrom, including, without limitation, small intestine submucosa (SIS), urinary bladder submucosa (UBS), stomach submucosa (SS), central nervous system tissue, epithelium of mesodermal origin, i.e., mesothelial tissue, dermal tissue, subcutaneous tissue, gastrointestinal tissue, tissue surrounding growing bone, placental tissue, omentum tissue, cardiac tissue, kidney tissue, pancreas tissue, lung tissue, and combinations thereof. The ECM can also comprise collagen from mammalian sources.

The terms "heart tissue" and "cardiac tissue" are used collectively herein, and mean and include, without limitation, mammalian tissue derived from any cardiovascular structure including, without limitation, pericardial tissue, myocardial tissue, vascular tissue and the like.

The terms "mammalian-based tissue", "collagenous mammalian tissue" and "collagenous tissue" are used collectively herein, and mean and include, without limitation, tissue that is also derived from a mammalian tissue source.

According to the invention, the mammalian-based tissue and collagenous mammalian tissue can similarly be derived from a variety of mammalian tissue sources and tissue derived therefrom, including, without limitation, the heart, small intestine, large intestine, stomach, lung, liver, kidney, pancreas, peritoneum, placenta, amniotic membrane, umbilical cord, bladder, prostate, and any fetal tissue from any mammalian organ.

The mammalian-based tissue and collagenous mammalian tissue can also be derived from a mammalian tissue source that is devoid of xenogeneic antigens, including, without limitation, collagenous mammalian tissue that is devoid of one of the following xenogeneic antigens: galactose-alpha-1,3-galactose (also referred to as α-gal), beta-1,4 N-acetylgalactosaminyltransferase 2, membrane cofactor protein, hepatic lectin H1, cytidine monophospho-N-acetyl-neuraminic acid hydroxylase, swine leukocyte antigen class I and porcine endogenous retrovirus polymerase (referred to herein as "immune privileged collagenous mammalian tissue").

The term "genetically modified organism", as used herein means and includes any living organism that has at least one gene modified by artificial means, e.g., gene editing.

The term "immune privileged collagenous mammalian tissue", as used herein means and includes xenogeneic collagenous mammalian tissue that can be disposed proximate mammalian tissue with a minimal or virtually absent adverse immune response; particularly, an adverse immune response associated with xenogeneic tissue graft rejection.

According to the invention, the term "mammalian" means and includes, without limitation, warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "crosslinked collagenous mammalian tissue", as used herein, means and includes mammalian tissue that exhibits at least 25% chemical bonding of adjacent chains of molecules, i.e., collagen fibrils, which comprise the collagenous mammalian tissue.

The term "polymer", as used herein means and includes, without limitation, polyurethane urea, porous polyurethane urea (Artelon®), polypropylene, poly(ε-caprolactone) (PCL), poly(glycerol sebacate) (PGS), polytetrafluoroethylene (PTFE), poly(styrene-block-isobutylene-block-Styrene) (SIBS), polyglycolide (PGA), polylactide (PLA), polydioxanone (a polyether-ester), polylactide-co-glycolide, polyamide esters, polyalkalene esters, polyvinyl esters, polyvinyl alcohol, polyanhydrides, polyurethanes, polydimethylsiloxanes, poly(ethylene glycol), polytetrafluoroethylene (Teflon™) and polyethylene terephthalate (Dacron™).

The term "natural polymer", as used herein means and includes, without limitation, polysaccharides (e.g., starch and cellulose), proteins (e.g., gelatin, casein, silk, wool, etc.), and polyesters (e.g., polyhydroxyalkanoates).

The term "biologically active agent", as used herein, means and includes an agent that induces or modulates a physiological or biological process, or cellular activity, e.g., induces proliferation, and/or growth and/or regeneration of tissue.

The term "biologically active agent" thus means and includes a growth factor, including, without limitation, fibroblast growth factor-2 (FGF-2), transforming growth factor beta (TGF-(β)) and vascular endothelial growth factor (VEGF).

The term "biologically active agent" also means and includes a cell, including, without limitation, human embryonic stem cells, myofibroblasts, mesenchymal stem cells, and hematopoietic stem cells.

The term "biologically active agent" also means and includes an exosome and/or microsome.

The terms "exosome" and "microsome" as used herein mean and include a lipid bilayer structure that contains or encapsulates a biologically active agent and/or pharmacological agent, including, without limitation, a growth factor, e.g., TGF-β, TGF-α, VEGF and insulin-like growth factor (IGF-I), a cytokine, e.g., interleukin-10 (IL-10), a transcription factor and microRNA (miRNA).

The term "biologically active agent" also means and includes agents commonly referred to as a "protein", "peptide" and "polypeptide", including, without limitation, collagen (types I-V), proteoglycans and glycosaminoglycans (GAGs).

The terms "pharmacological agent", "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent" and "drug" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPs), enzymes and enzyme inhibitors, anticoagulants and/or anti-thrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent" and "drug" also mean and include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), NT-3, NT-4, NGF and IGF-2.

The terms "pharmacological agent", "active agent" and "drug" also mean and include the Class I-Class V antiarrhythmic agents disclosed in Applicant's U.S. Pat. Nos. 9,119,841, 10,188,509, 10,188,510 and 10,143,778, and Co-pending application Ser. Nos. 16/129,968 and 16/990,236, including, without limitation, (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent" and "drug" also mean and include, without limitation, the antibiotics disclosed in Applicant's U.S. Pat. Nos. 9,119,841, 10,188,509, 10,188,510 and 10,143,778, and Co-pending application Ser. Nos. 16/129,968 and 16/990,236, including, without limitation, aminoglycosides, cephalosporins, chloramphenicol, clindamycin, erythromycins, fluoroquinolones, macrolides, azolides, metronidazole, penicillin, tetracyclines, trimethoprim-sulfamethoxazole, gentamicin and vancomycin.

As indicated above, the terms "pharmacological agent", "active agent" and "drug" also mean and include an anti-inflammatory.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e., the protective tissue response to injury or destruction of tissues, which serves to destroy, dilute, or wall off both the injurious agent and the injured tissues.

The terms "anti-inflammatory" and "anti-inflammatory agent" thus include the anti-inflammatories disclosed in Applicant's U.S. Pat. Nos. 9,119,841, 10,188,509, 10,188,510 and 10,143,778, and Co-pending application Ser. Nos. 16/129,968 and 16/990,236, including, without limitation, desoximetasone, dexamethasone dipropionate, cloticasone propionate, diftalone, fluorometholone acetate, fluquazone, meseclazone, mesterolone, methandrostenolone, methenolone, methenolone acetate, methylprednisolone suleptanate, halopredone acetate, alclometasone dipropionate, apazone, balsalazide disodium, cintazone cormethasone acetate, cortodoxone, diflorasone diacetate, diflumidone sodium, endrysone, fenpipalone, flazalone, fluretofen, fluticasone propionate, isoflupredone acetate, nabumetone, nandrolone, nimazone, oxyphenbutazone, oxymetholone, phenbutazone, pirfenidone, prifelone, proquazone, rimexolone, seclazone, tebufelone and testosterone.

The terms "pharmacological agent", "active agent" and "drug" also mean and include the statins, i.e., HMG-CoA reductase inhibitors, disclosed in Applicant's U.S. Pat. Nos. 9,119,841, 10,188,509, 10,188,510 and 10,143,778, and Co-pending application Ser. Nos. 16/129,968 and 16/990,236, including, without limitation, atorvastatin, cerivastatin, fluvastatin and lovastatin.

The terms "pharmacological agent", "active agent", "drug" and "active agent formulation" further mean and include the anti-proliferative agents disclosed in Applicant's U.S. Pat. Nos. 9,119,841, 10,188,509, 10,188,510 and 10,143,778, and Co-pending application Ser. Nos. 16/129,968 and 16/990,236, including, without limitation, paclitaxel, sirolimus and derivatives thereof, including everolimus.

The term "pharmacological composition", as used herein, means and includes a composition comprising a "pharmacological agent" and/or any additional agent or component identified herein.

Additional biologically active and pharmacological agents are set forth in priority U.S. application Ser. No. 15/206,833, now U.S. Pat. No. 10,188,510, which is expressly incorporated herein in its entirety.

The term "therapeutically effective", as used herein, means that the amount of the "pharmacological agent" and/or "biologically active agent" and/or "pharmacological composition" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The term "comprise" and variations of the term, such as "comprising" and "comprises," as used in connection with a prosthetic valve composition and/or mammalian tissue, also means a composition and/or mammalian tissue employed to form a prosthetic valve structure, such as a sheet member, and, hence, a prosthetic valve of the invention.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to prosthetic heart valves that can be readily employed to selectively replace diseased or defective heart valves, and methods for attaching (or anchoring) same to cardiovascular structures and/or tissue.

In some embodiments of the invention, the prosthetic valves comprise continuous conical shaped sheet members or structures.

In some embodiments of the invention, the sheet structures and, thereby, prosthetic valves formed therefrom comprise ribbon structures.

In some embodiments, the sheet members and, thereby, prosthetic valves formed therewith comprise seamless ribbon structures that are formed from pre-formed sheet structures, such as the sheet members disclosed in Co-Pending U.S. application Ser. No. 16/440,504, which is incorporated by reference herein in its entirety.

According to the invention, the sheet structures and, thereby, prosthetic valves formed therewith, can comprise a single sheet structure or multiple sheet structures, e.g., two sheet structures, three sheet structures, etc.

Suitable single sheet and multiple sheet structures are disclosed in Applicant's U.S. Pat. No. 10,143,778, which is incorporated by reference herein in its entirety.

As indicated above, in a preferred embodiment, the sheet members and, thereby, prosthetic valves formed therewith, comprise a plurality of elongated ribbon members.

In a preferred embodiment, the sheet members and, thereby, prosthetic valves formed therewith, comprise a plurality of fluid flow modulating regions, which transition from an open fluid flow configuration to a closed fluid flow configuration in response to expansion and contraction of the sheet members.

As also indicated above, in a preferred embodiment, the prosthetic valves further comprise a support structure that facilitates engagement of the valves to cardiovascular structures.

In a preferred embodiment, the support structure is also adapted or configured to reinforce the valves when disposed therein and position the valves proximate a cardiovascular structure, e.g., valve annulus (and, hence, cardiovascular tissue associated therewith) and maintain contact therewith for a pre-determined period of time.

In a preferred embodiment, the support structure comprises an expandable annular ring that is adapted to transition from a pre-deployment configuration, whereby the annular ring and valve associated therewith can be positioned proximate a target cardiovascular structure, e.g., a valve annulus, to an expanded, post-deployment configuration, whereby the annular ring and valve associated therewith is positioned proximate tissue associated with the target cardiovascular structure.

As discussed in detail herein, the annular ring can comprise various configurations.

In some embodiments of the invention, the annular ring comprises a microneedle anchoring mechanism that is configured to engage tissue of a cardiovascular structure, position a prosthetic valve associated therewith proximate the cardiovascular structure and maintain contact of the valve to the cardiovascular tissue for a pre-determined period of time.

Suitable annular rings are disclosed in Applicant's U.S. Pat. Nos. 9,044,319, 10,188,509, 10,188,510 and 10,052,409, which are incorporated by reference herein in their entirety.

According to the invention, the prosthetic valves of the invention can further comprise a structural ring and/or supplemental support structure, such as also disclosed in Applicant's U.S. Pat. Nos. 10,188,510 and 10,052,409.

According to the invention, the prosthetic valves and support structures can comprise various biocompatible materials and compositions.

As indicated above, in a preferred embodiment, the prosthetic valves comprise mammalian-based tissue.

In some embodiments of the invention, the mammalian-based tissue comprises an ECM composition comprising acellular ECM from a mammalian tissue source.

According to the invention, the ECM can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508; which are incorporated by reference herein in their entirety.

As indicated above, according to the invention, suitable mammalian tissue sources include, without limitation, the small intestine, large intestine, stomach, lung, liver, kidney, pancreas, peritoneum, placenta, heart, bladder, prostate, tissue surrounding growing enamel, tissue surrounding growing bone, and any fetal tissue from any mammalian organ.

The mammalian tissue can thus comprise, without limitation, small intestine submucosa (SIS), urinary bladder submucosa (UBS), stomach submucosa (SS), central nervous system tissue, epithelium of mesodermal origin, i.e., mesothelial tissue, dermal tissue, subcutaneous tissue, gastrointestinal tissue, placental tissue, omentum tissue, cardiac tissue, kidney tissue, pancreas tissue, lung tissue, and combinations thereof. The ECM can also comprise collagen from mammalian sources.

In some embodiments, the mammalian-based tissue comprises collagenous mammalian tissue derived from a mammalian tissue source.

In some embodiments of the invention, the mammalian-based tissue is decellularized.

According to the invention, the collagenous mammalian tissue can be similarly be derived from a variety of mammalian tissue sources and tissue derived therefrom, including, without limitation, the heart, small intestine, large intestine, stomach, lung, liver, kidney, pancreas, peritoneum, placenta, amniotic membrane, umbilical cord, bladder, prostate, and any fetal tissue from any mammalian organ.

In some embodiments of the invention, the collagenous mammalian tissue comprises pericardium tissue.

In some embodiments of the invention, the mammalian tissue source comprises a bovine tissue source, e.g., bovine pericardium tissue.

In some embodiments of the invention, the mammalian tissue source comprises a porcine tissue source, e.g., porcine pericardium tissue.

In some embodiments, the collagenous mammalian tissue comprises crosslinked collagenous mammalian tissue.

In some embodiments, the mammalian tissue source comprises an adolescent mammalian tissue source, i.e., tissue derived from a mammal less than 3 years of age.

In some embodiments of the invention, the collagenous mammalian tissue is derived from a mammalian tissue source that is devoid of xenogeneic antigens.

In some embodiments, the collagenous mammalian tissue thus comprises collagenous mammalian tissue that is devoid of one of the following xenogeneic antigens: galactose-alpha-1,3-galactose (also referred to as α-gal), beta-1,4 N-acetylgalactosaminyl-transferase 2, membrane cofactor protein, hepatic lectin H1, cytidine monophospho-N-acetyl-neuraminic acid hydroxylase, swine leukocyte antigen class I and porcine endogenous retrovirus polymerase (referred to hereinafter as "immune privileged collagenous mammalian tissue").

In some embodiments, the immune privileged collagenous mammalian tissue is derived from a genetically modified organism, such as, by way of example, a genetically modified pig and/or bovine.

In some embodiments, the immune privileged collagenous mammalian tissue is thus derived from a genetically modified pig.

In some embodiments, the genetically modified pig comprises a pig originating from at least one porcine germline cell, e.g., embryo, that has been genetically altered or reconstructed to knockout or delete at least one porcine gene that encodes for a xenogeneic antigen product.

According to the invention, the genetic alteration or reconstruction of a germline cell; more specifically, a porcine embryo can be done according to any conventional gene editing method, such as conventional gene editing methods that employ clustered regularly interspaced short palindromic repeats (CRISPR)-Cas9, Transcription Activator-like Effector Nucleases (TALEN) or RNA interference.

In some embodiments, the knockout or deletion of a gene in a porcine embryo and, hence, pig developed therefrom is done according to the CRISPR-Cas9 gene editing method described in Niu, et al., *Inactivation of Porcine Endogenous Retrovirus in Pigs Using CRISPR-Cas9*, Science, vol. 357, no. 6357, pp. 1303-1307 (2017), which is incorporated by reference herein in its entirety.

According to the invention, the noted gene editing methods can be adapted and configured to knockout or delete any genes in a porcine embryo that encode for xenogeneic antigens including, without limitation, GGTA1 (galactose-alpha-1,3-galactose), β4GalNT2 (beta-1,4 N-acetylgalactosaminyltransferase 2), CD46 (membrane cofactor protein), ASGR1 (hepatic lectin H1), CMAH (cytidine monophospho-N-acetylneuraminic acid hydroxylase), SLA class I (swine leukocyte antigen class I) and PERV pol (porcine endogenous retrovirus polymerase) gene.

In some embodiments, the collagenous mammalian tissue is derived from mammalian tissue of a pig developed from an embryo that has been genetically altered by knocking out or deleting the genes GGTA1, β4GalNT2 and CMAH, which encode for the xenogeneic antigen products galactose-alpha-1,3-galactose, beta-1,4 N-acetylgalactosaminyltransferase 2 and cytidine monophospho-N-acetylneuraminic acid hydroxylase, respectively.

According to the invention, the likelihood of inducing an adverse immune response, including adverse immune responses associated with xenogeneic tissue graft rejection, in vivo with the above referenced immune privileged collagenous mammalian tissue is minimal.

As indicated above and set forth in Priority Co-Pending U.S. application Ser. Nos. 16/129,968 and 16/440,504, in some embodiments of the invention, the prosthetic valves of the invention are formed from and, hence, comprise a polymeric composition comprising at least one polymer; preferably, a biocompatible polymer.

According to the invention, suitable biocompatible polymers include, without limitation, polyurethane urea, including porous polyurethane urea (Artelon®), polypropylene, poly(ε-caprolactone) (PCL), poly(glycerol sebacate) (PGS), polytetrafluoroethylene (PTFE), poly(styrene-block-isobutylene-block-Styrene) (SIBS), polyglycolide (PGA), polylactide (PLA), polydioxanone (a polyether-ester), polylactide-co-glycolide, polyamide esters, polyalkalene esters, polyvinyl esters, polyvinyl alcohol, polyanhydrides, polyurethanes, polydimethylsiloxanes, poly(ethylene glycol), polytetrafluoroethylene (Teflon™), and polyethylene terephthalate (Dacron™), and combinations thereof.

As also indicated above, in some embodiments of the invention, the mammalian-based tissue and/or polymeric composition (and, hence, prosthetic valves formed therefrom) further comprises at least one additional biologically active agent or composition, i.e., an agent that induces or modulates a physiological or biological process, or cellular activity, e.g., induces proliferation, and/or growth and/or regeneration of tissue.

According to the invention, suitable biologically active agents include any of the aforementioned biologically active agents.

In some embodiments of the invention, the biologically active agent comprises a growth factor, including, without limitation, transforming growth factor beta (TGF-β), fibroblast growth factor-2 (FGF-2), and vascular endothelial growth factor (VEGF).

As also indicated above, in some embodiments of the invention, the mammalian-based tissue and/or polymeric composition (and, hence, prosthetic valves formed therefrom) further comprises at least one pharmacological agent or composition (or drug), i.e., an agent or composition that is capable of producing a desired biological effect in vivo, e.g., stimulation or suppression of apoptosis, stimulation or suppression of an immune response, etc.

According to the invention, suitable pharmacological agents and compositions include any of the aforementioned pharmacological agents and agents set forth in Applicant's U.S. Pat. No. 10,188,510.

It is thus contemplated that, in some embodiments of the invention, following placement of a prosthetic valve of the invention, on or in a cardiovascular structure (or structures) of a subject, e.g., valve annulus, and, hence, proximate damaged cardiovascular tissue associated therewith, the prosthetic valve will induce or modulates a physiological or biological process, or cellular activity, e.g., induces proliferation, and/or growth and/or regeneration of tissue.

It is further contemplated that, in some embodiments of the invention, following placement of a prosthetic valve of the invention, on or in a cardiovascular structure (or structures) of a subject, e.g., valve annulus, and, hence, proximate damaged cardiovascular tissue associated therewith, the prosthetic valve will induce a desired biological effect in vivo, e.g., stimulation or suppression of apoptosis, stimulation or suppression of an immune response, etc.

It is further contemplated that, following placement of a prosthetic valve of the invention comprising an ECM composition (i.e., an ECM tissue valve), on or in a cardiovascular structure (or structures) of a subject, e.g., valve annulus, and, hence, proximate damaged cardiovascular tissue associated therewith, the ECM tissue valve will become populated with endogenous cells that will gradually remodel the ECM tissue into cardiovascular tissue and tissue (and, hence, valve) structures.

It is further contemplated that, following placement of an ECM tissue valve of the invention on or in a cardiovascular structure (or structures) of a subject, and, hence, proximate damaged cardiovascular tissue associated therewith, stem cells will migrate to the ECM tissue valve from the point(s) at which the valve is attached to the cardiovascular structure or structures.

It is still further contemplated that, during circulation of epithelial and endothelial progenitor cells after placement of an ECM tissue valve of the invention on a cardiovascular structure (or structures), the surfaces of an ECM tissue valve will rapidly become lined or covered with epithelial and/or endothelial progenitor cells.

It is still further contemplated that, in some embodiments, the points at which an ECM tissue valve of the invention is attached to a cardiovascular structure (or structures) in a subject will serve as points of constraint that direct remodeling of the ECM into cardiovascular tissue and valve structures that are identical or substantially identical to properly functioning native cardiovascular tissue and valve structures.

It is still further contemplated that, in some embodiments, following placement of a prosthetic valve of the invention on or in a cardiovascular structure (or structures) in a subject and, hence, proximate cardiovascular tissue associated therewith, the prosthetic valve will induce "modulated healing" of the cardiovascular structure(s) and cardiovascular tissue associated therewith.

The term "modulated healing", as used herein, and variants of this language generally refer to the modulation (e.g., alteration, delay and retardation) of a process involving different cascades or sequences of naturally occurring tissue repair in response to localized tissue damage or injury, substantially reducing their inflammatory effect.

Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments of the invention, a prosthetic valve of the invention is specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase when in contact with biological tissue.

In some embodiments, "modulated healing" means and includes the ability of a prosthetic valve of the invention to restrict the expression of inflammatory components. By way of example, according to the invention, when an ECM tissue valve of the invention comprises a statin augmented ECM composition, i.e., a composition comprising ECM and a statin, and the ECM tissue valve is positioned proximate damaged biological tissue, e.g., attached to a valve annulus, the ECM tissue valve restricts expression of monocyte chemoattractant protein-1 (MCP-1) and chemokine (C-C) motif ligand 2 (CCR2).

In some embodiments of the invention, "modulated healing" means and includes the ability of a prosthetic valve of the invention, such as, for example, an ECM tissue valve or a prosthetic tissue valve comprising an antibiotic augmented polymeric composition, to alter a substantial inflammatory phase (e.g., platelet or fibrin deposition) at the beginning of the tissue healing process. As used herein, the phrase "alter a substantial inflammatory phase" refers to the ability of a prosthetic tissue valve of the invention to substantially reduce the inflammatory response at a damaged tissue site, e.g., valve annulus, when in contact with tissue at the site.

In such an instance, a minor amount of inflammation may ensue in response to tissue injury, but this level of inflammation response, e.g., platelet and/or fibrin deposition, is substantially reduced when compared to inflammation that takes place in the absence of a prosthetic tissue valve of the invention.

The term "modulated healing" also refers to the ability of a prosthetic valve of the invention, particularly, an ECM tissue valve, to induce host tissue proliferation, bioremodeling, including neovascularization, e.g., vasculogenesis, angiogenesis, and intussusception, and regeneration of new tissue and tissue structures with site-specific structural and functional properties, when disposed proximate damaged tissue of a cardiovascular structure, e.g., a valve annulus.

Thus, in some embodiments of the invention, the term "modulated healing" means and includes the ability of a prosthetic valve of the invention, particularly, an ECM tissue valve, to modulate inflammation and induce host tissue proliferation and remodeling, and regeneration of new tissue when disposed proximate damaged tissue.

In some embodiments of the invention, the ECM composition further comprises a biologically active agent comprising an exosome (referred to hereinafter as an "exosome augmented ECM composition").

As discussed in detail in Applicant's U.S. application Ser. No. 15/386,640, now U.S. Pat. No. 10,143,778, which is incorporated by reference herein, exosomes significantly enhance modulated healing induced by a prosthetic valve of the invention, particularly, an ECM tissue valve, through several properties/capabilities.

A first seminal property is the capacity of exosomes to generate and provide an exosome lipid bilayer that shields bioactive molecules, e.g., biologically active agents, from proteolytic agents, which can, and often will, degrade unshielded (or free) bioactive molecules and render the molecules non-functional in biological tissue environments.

Exosomes also facilitate and enhance direct interaction by and between bioactive molecules; particularly, biologically active agents and endogenous cells (and, hence, direct delivery of bioactive molecules to endogenous cells) in biological tissue, which enhances the bioactivity of the agents.

Thus, it is contemplated that, in some embodiments of the invention, following placement of a prosthetic valve of the invention; particularly, an ECM tissue valve comprising an exosome augmented ECM composition, on or in a cardiovascular structure (or structures) of a subject, e.g., valve annulus, and, hence, proximate damaged cardiovascular tissue associated therewith, the ECM tissue valve will induce a multitude of significant biological processes in vivo, including significantly enhanced inflammation modulation of the cardiovascular tissue, and significantly induced neovascularization, stem cell proliferation, remodeling of the cardiovascular tissue, and regeneration of new tissue and tissue structures.

By way of example, when an exosome augmented ECM composition comprising encapsulated IL-8 (and, hence, an ECM tissue valve formed therefrom) is disposed proximate damaged cardiovascular tissue, the exosome augmented ECM composition and, hence, ECM tissue valve formed therefrom, modulates the transition of M1 type "acute inflammatory" macrophages to M2 type "wound healing" macrophages initiated by the acellular ECM.

By way of further example, when an exosome augmented ECM composition comprising encapsulated miRNAs (and, hence, an ECM tissue valve formed therefrom) is disposed proximate damaged cardiovascular tissue, the exosome augmented ECM composition and, hence, tissue valve formed therefrom induce enhanced stem cell proliferation via the delivery of exosome encapsulated miRNAs and transcription factors to the damaged cardiovascular tissue, which signals the endogenous stem cells to bind and/or attach to the acellular ECM and proliferate.

As indicated above, in a preferred embodiment of the invention, the prosthetic valves comprise a support structure that facilitates engagement of the valves to cardiovascular tissue and associated cardiovascular structures.

In some embodiments, the support structure is further designed and configured to reinforce the prosthetic valves, i.e., enhance the structural integrity of the valves, and (ii) preferably position the prosthetic valves proximate a cardiovascular structure, e.g., valve annulus (and, hence, cardiovascular tissue associated therewith) and maintain contact therewith for a pre-determined period of time.

According to the invention, the support structure can comprise various biocompatible materials.

In some embodiments of the invention, the support structure thus comprises a biocompatible metal.

According to the invention, suitable biocompatible metals comprise, without limitation, a shape memory nickel-titanium, such as Nitinol®, titanium, stainless steel and magnesium.

In some embodiments, the support structure comprises one of the aforementioned polymeric compositions.

In some embodiments, the support structure comprises one of the aforementioned ECM compositions.

According the invention, the support structure can further comprise a composition comprising a mixture of at least one of the aforementioned polymers and one of the aforementioned ECM materials.

In a preferred embodiment of the invention, the support structure comprises comprise Dyneema®, a high strength, ultra-high molecular weight polyethylene (UHMwPE).

In some embodiments of the invention, the support structure includes an outer coating. As discussed in detail below, the coating can comprise, without limitation, an immunomodulating compound that suppresses adverse immune responses.

In some embodiments, the immunomodulating compound also induces regenerative immune responses associated with host tissue proliferation, bioremodeling and regeneration of new tissue and tissue structures with site-specific structural and functional properties.

In some embodiments, the immunomodulating compound comprises a polysaccharide, including without limitation, a GAG, a dextran, alginate and chitosan.

In some embodiments, immunomodulating compound comprises a polymeric material, including, without limitation, high molecular weight hyaluronic acid (HMW-HA).

In some embodiments, the coating comprises one of the aforementioned ECM compositions.

In some embodiments, the coating comprises one of the aforementioned polymeric compositions.

In some embodiments, the noted coating compositions comprise at least one of the aforementioned biologically active agents and/or pharmacologically active agents.

In some embodiments, the noted coating compositions comprise an anti-proliferative agent, such as sirolimus.

Figure 2A:
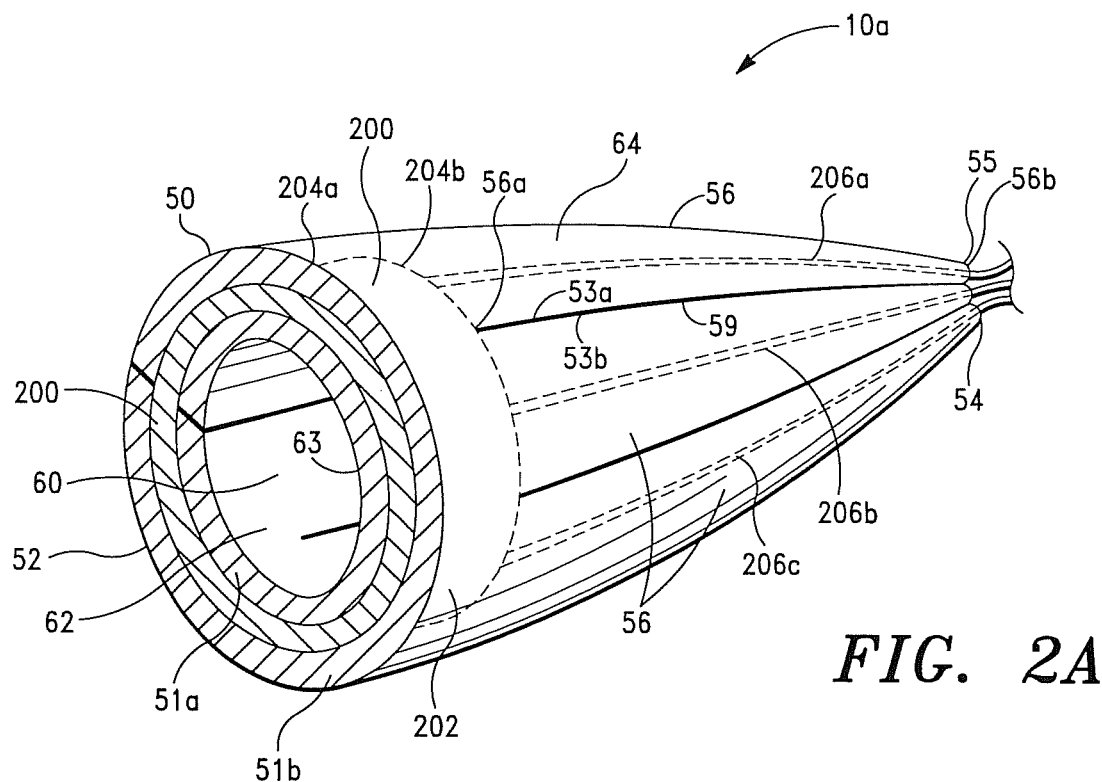
FIG. 2A is a perspective, partial sectional view of one embodiment of a reinforced prosthetic "ribbon structure" valve, in accordance with the invention.
Figure 2B:
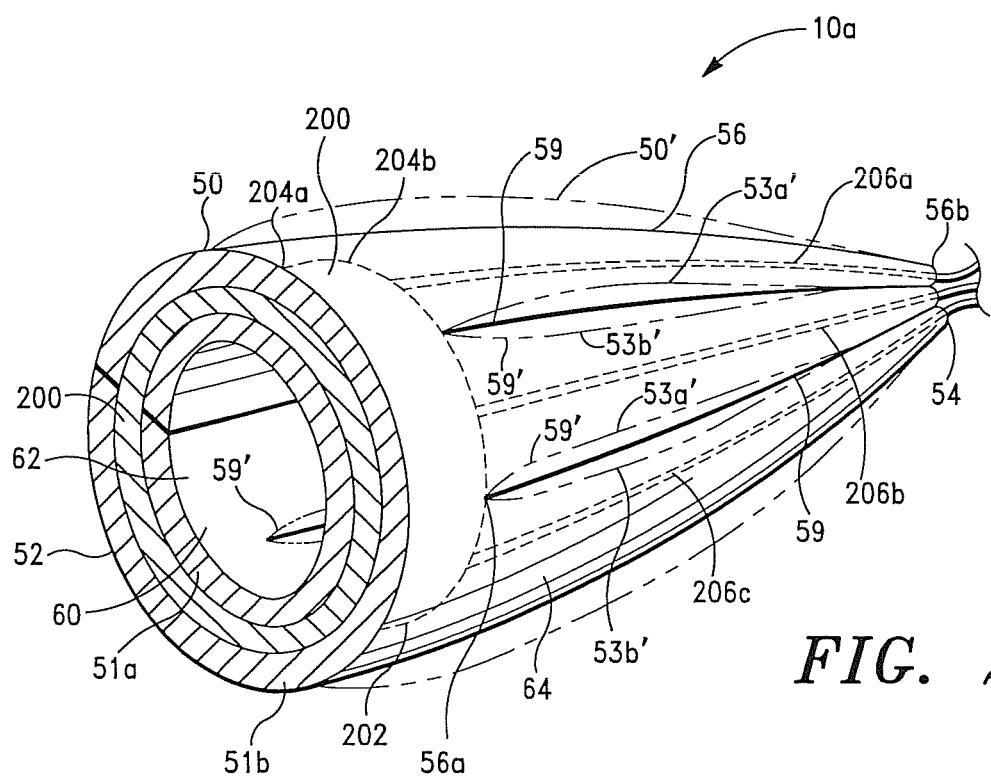
FIG. 2B is a further perspective, partial sectional view of the prosthetic valve shown in FIG. 2A, illustrating one embodiment of fluid flow modulating regions thereof in open and closed configurations, in accordance with the invention.

Referring now to FIGS. 2A and 2B, there is shown one embodiment of a prosthetic "ribbon structure" valve of the invention (denoted "10a"), where FIG. 2B illustrates the fluid flow modulating regions of prosthetic valve 10a in open and closed configurations.

As illustrated in FIGS. 2A and 2B, in a preferred embodiment of the invention, the prosthetic valve 10a comprises a base member 50 comprising at least two (2) prosthetic valve sheet layers 51a, 51b, an interior region 60, a valve lumen 63, inner and outer surfaces 62, 64, a proximal valve annulus engagement end 52 and a distal end 54.

As set forth in Co-Pending U.S. application Ser. Nos. 16/440,504 and 16/129,968, which are incorporated by reference herein, the proximal valve annulus engagement end 52 of the prosthetic valve 10a (and prosthetic tissue valves 10b-10d, discussed herein) can comprise a circumference, i.e., operative valve annulus engagement end circumference, in the range of approximately 20 mm to 220 mm.

The prosthetic valve 10a (and prosthetic tissue valves 10b-10d) can also comprise a length in the range of approximately 15 mm to 150 mm. In some embodiments of the invention, the prosthetic valve 10a (and prosthetic tissue valves 10b-10d) has a length in the range of approximately 10 mm to 100 mm.

The prosthetic valve 10a (and prosthetic tissue valves 10b-10d) thus preferably has a "balanced" valve annulus engagement end circumference to valve length ratio in the range of approximately 1:1-2:1.

The noted prosthetic valve dimensions; particularly, the valve annulus engagement end circumference to length ratio, are deemed important for effective operability of the prosthetic tissue 10a (and prosthetic tissue valves 10b-10d), i.e., effective fluid flow modulation therethrough as a function of the fluid, i.e., blood, flow pressure differential in the valve(s) resulting from a typical in vivo cardiac blood flow pressure gradient across a valve annulus in the range of approximately 1-5 mm Hg.

As also set forth in Co-Pending U.S. application Ser. Nos. 16/440,504 and 16/129,968, which are incorporated by reference herein, and illustrated in FIGS. 2A and 2B, the base member 50 further comprises a plurality of ribbon members or ribbons 56 that extend from the proximal valve annulus engagement end 52 to the distal end 54 of the base member 50.

Referring back to FIGS. 2A and 2B, the ribbons 56 of the formed prosthetic valve 10a preferably taper to a substantially coincident point 55, wherein the base member 50 has a substantially conical shape.

As also set forth in Co-Pending U.S. application Ser. Nos. 16/440,504 and 16/129,968, the distal ends 56b of the ribbons 56 are in a joined relationship, wherein fluid flow through the joined distal ends 56b of the ribbons 56 is restricted.

As further illustrated in FIGS. 2A and 2B, the ribbons 56 extend circumferentially from the proximal end 52 of the base member 50, wherein the first edge regions 53a and the second edge regions 53b of the ribbons 56 are positioned adjacent each other and form a plurality of fluid flow modulating regions 59.

Referring now to FIG. 2B, in a preferred embodiment, the base member 50 is configured to expand during fluid flow comprising a first fluid flow pressure through the base member 50, as shown in phantom and denoted 50', and contract when the fluid flow through the base member 50 comprises a second fluid flow pressure, the second fluid flow pressure being lower than the first fluid flow pressure.

As further set forth in Co-Pending U.S. application Ser. Nos. 16/440,504 and 16/129,968 and shown in FIG. 2B, the fluid flow modulating regions 59 are configured to open during expansion of the base member 50' (as shown in phantom and denoted 59'), i.e., the first and second edge regions 53a, 53b separate, as shown in phantom and denoted 53a', 53b', wherein the fluid flow is allowed to be transmitted through the fluid flow modulating regions 59', and close during the contraction of the base member 50, wherein the fluid flow through base member 50 is restricted, more preferably, abated.

As indicated above and further illustrated in FIGS. 2A and 2B, in a preferred embodiment of the invention, the prosthetic valve 10a also comprises a support structure 200 that facilitates engagement of prosthetic valve 10a to cardiovascular structures.

In a preferred embodiment, the support structure 200 is disposed or positioned between the prosthetic valve sheet layers 51a, 51b.

According to the invention, the support structure 200 can also be disposed in the interior region 60, i.e., valve lumen 63 of the valve 10a proximate the inner surface 62 thereof.

As discussed in detail below and illustrated in FIGS. 2A and 2B, in a preferred embodiment, the support structure 200 comprises an annular ring 202 comprising proximal and distal end regions 204a, 204b, and a plurality of elongated cardiovascular structure engagement members 206a, 206b, 206c that are in communication with and extend outwardly from the distal end region 204b of the annular ring 202.

According to the invention, the support structure 200 can comprise any number of cardiovascular structure engagement members. In some embodiments, the support structure 200 comprises at least one cardiovascular structure engagement member for every ribbon 56 of the valve 10a.

In a preferred embodiment, the cardiovascular structure engagement members 206a, 206b, 206c are similarly disposed between prosthetic valve sheet layers 51a, 51b that form the ribbons 56 of prosthetic valve 10a.

According to the invention, the cardiovascular structure engagement members 206a, 206b, 206c can also be disposed or positioned in the interior region 60 or proximate the outer surface of prosthetic valve 10a.

In a preferred embodiment of the invention, when the support structure 200 is operatively positioned in the interior region 60 of prosthetic valve 10a, the cardiovascular structure engagement members 206a, 206b, 206c are configured and have sufficient length to extend outwardly from the distal ends 56b of the ribbons 56 and, hence, from the distal end 54 of the valve 10a.

Figure 2C:
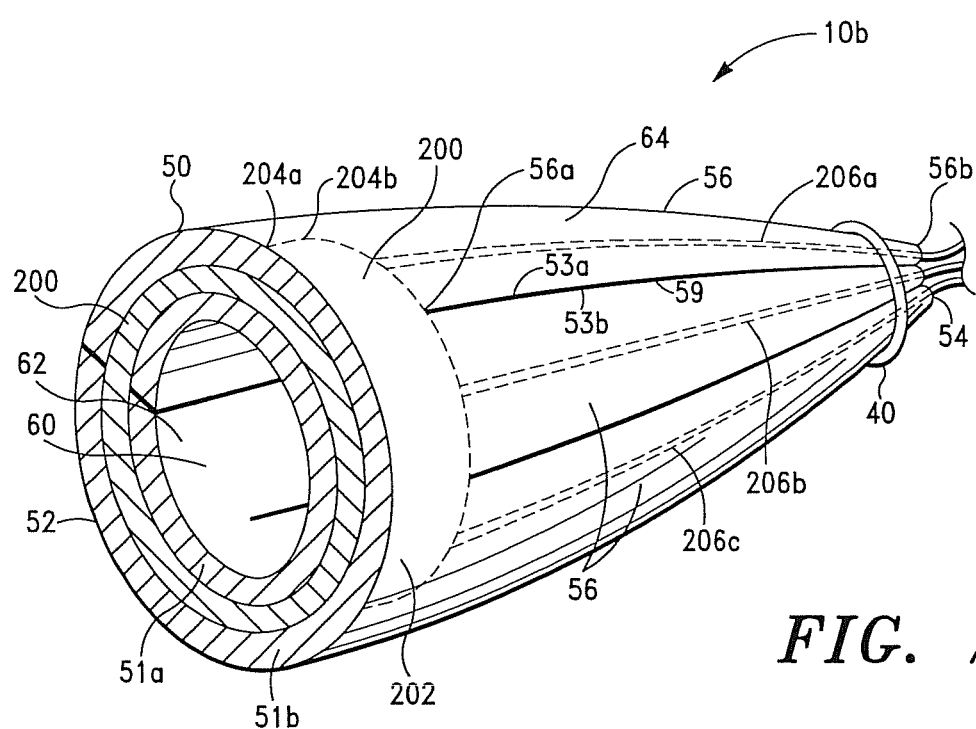
FIG. 2C is a perspective, partial sectional view of the prosthetic valve shown in FIG. 2A having a structural ring disposed at the distal end of the valve, in accordance with the invention.

Referring now to FIG. 2C, there is shown another embodiment of prosthetic valve 10a shown in FIGS. 2A and 2B. As illustrated in FIG. 2C, the prosthetic valve, now denoted 10b, includes a structural ring 40, such as described in Co-Pending U.S. application Ser. Nos. 16/440,504 and 16/129,968.

In a preferred embodiment, the structural ring 40 is sized and configured to be placed on the distal end 54 of prosthetic valve 10b and receive ribbons 56 therein, whereby the ribbons 56 are maintained in close proximity to each other, as shown in FIG. 2C.

Figure 3A:
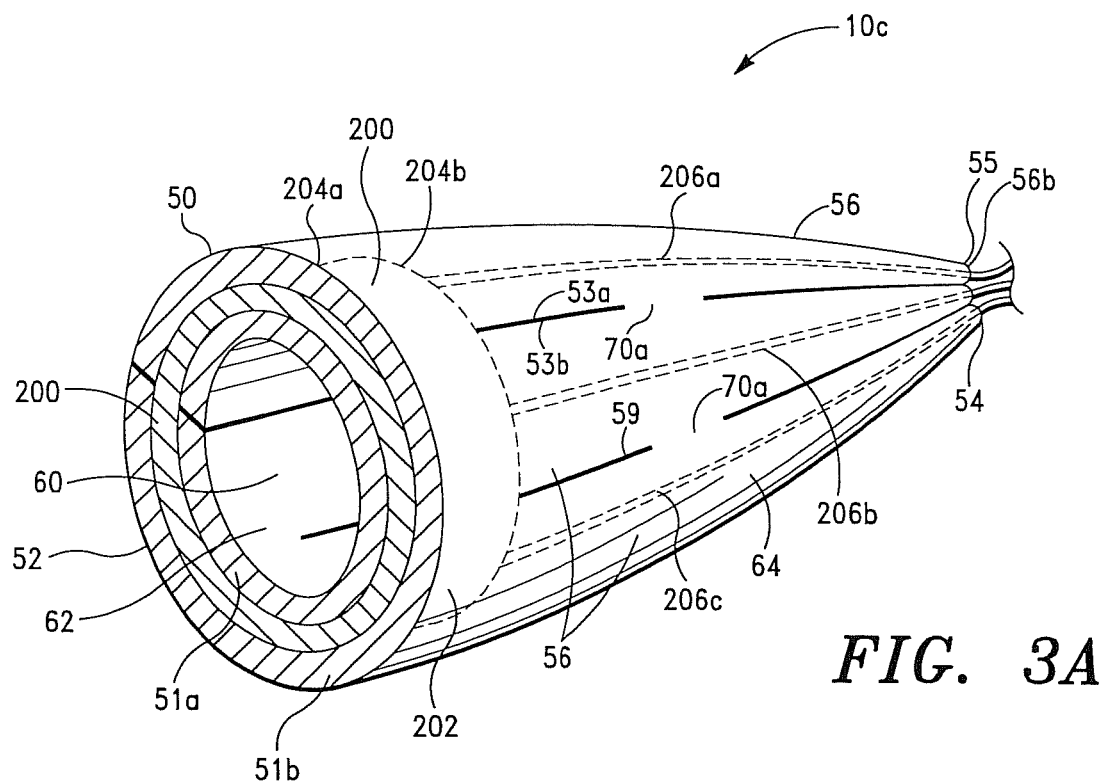
FIG. 3A is a perspective, partial sectional view of another embodiment of a reinforced prosthetic "ribbon structure" prosthetic valve having an integral ribbon coupling region, in accordance with the invention.
Figure 3B:
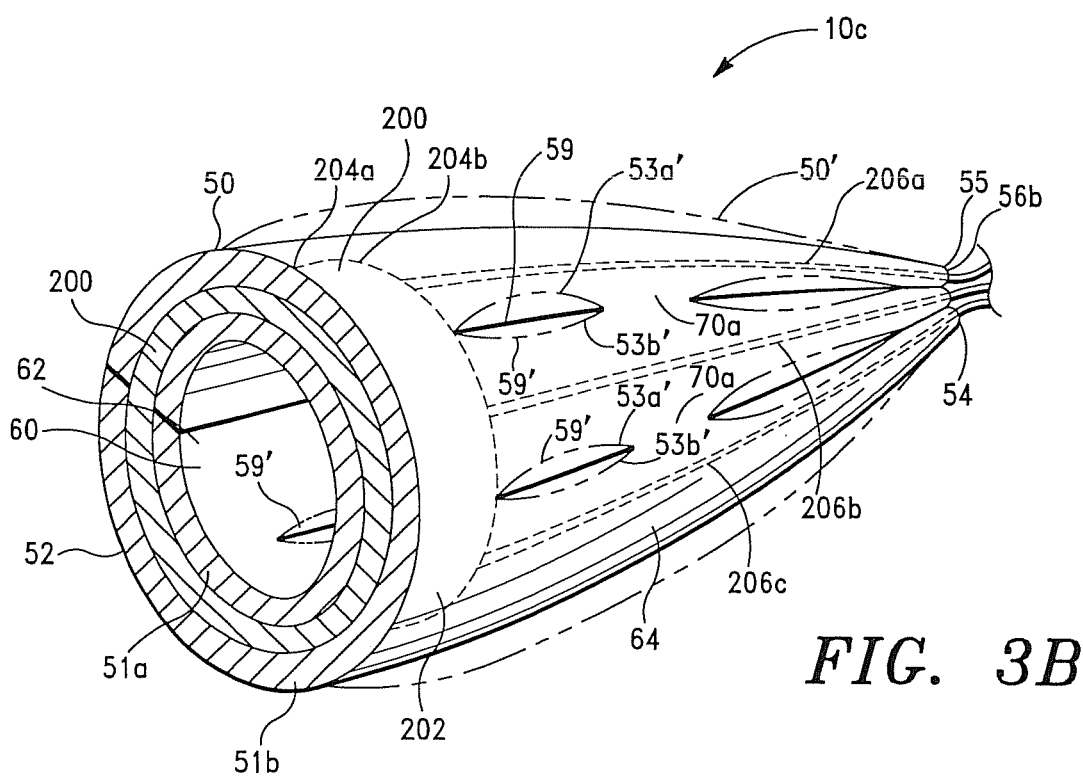
FIG. 3B is a further perspective, partial sectional view of the prosthetic valve shown in FIG. 3A, illustrating one embodiment of fluid flow modulating regions thereof in open and closed configurations, in accordance with the invention.

Referring now to FIGS. 3A and 3B there is shown a further embodiment of a prosthetic "ribbon structure" valve (denoted "10c"), which is also discussed in detail in Applicant's Co-Pending U.S. application Ser. Nos. 16/440,504 and 16/129,968.

As illustrated in FIGS. 3A and 3B, the prosthetic valve 10c similarly comprises a base member 50 comprising a proximal valve annulus engagement end 52 and a distal end 54. The base member 50 further comprises a plurality of ribbon members or ribbons 56 that are connected to and extend from the proximal end 52.

As further illustrated in FIGS. 3A and 3B, the prosthetic valve 10c further comprises a plurality of constraining or coupling regions (or members) 70a. As set forth in Co-Pending U.S. application Ser. Nos. 16/440,504 and 16/129,968, the coupling regions are sized and configured to couple (or join) a ribbon 56 to adjacent ribbons, i.e., couple a first edge region 53a of a first ribbon 56 to the second edge region 53b of a second ribbon 56, at a predetermined region.

As also set forth in Co-Pending U.S. application Ser. Nos. 16/440,504 and 16/129,968, the prosthetic valve 10c modulates fluid flow therethrough and, hence, through a valve annulus region when engaged thereto in a similar manner as prosthetic valve 10a, discussed above.

Figure 3C:
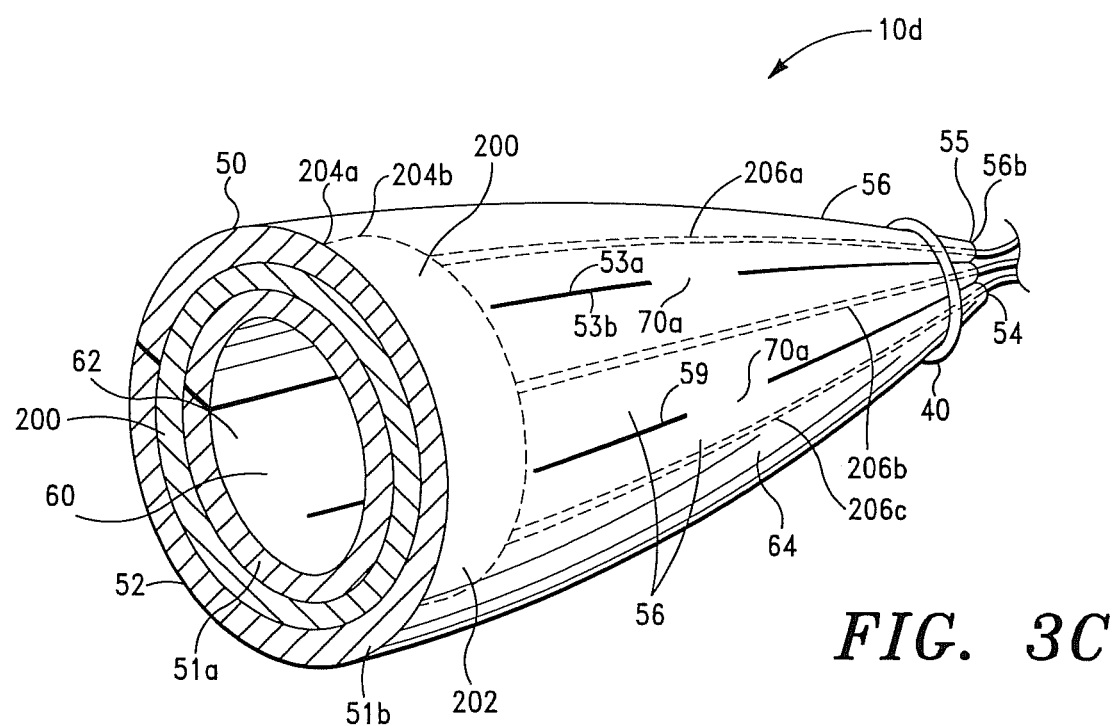
FIG. 3C is a perspective, partial sectional view of the prosthetic valve shown in FIG. 3A having a structural ring disposed at the distal end of the valve, in accordance with the invention.

As further set forth in Co-Pending U.S. application Ser. Nos. 16/440,504 and 16/129,968 and shown in FIG. 3C, the prosthetic valve (now denoted "10d") can also comprise a structural ring 40.

Referring now to FIGS. 4A through 10C, the support structures of the invention will be described in detail.

Support Structure Annular Rings

As indicated above, according to the invention, the support structure annular rings can comprise various configurations.

Referring now to FIGS. 4A and 4B, there is shown one embodiment of an annular ring of the invention (denoted "210").

As illustrated in FIGS. 4A and 4B, the annular ring 210, which is also disclosed and discussed in detail in Applicant's U.S. Pat. No. 9,044,319, preferably comprises a helical band element 212 that is adapted to transition from a "contracted" pre-deployment configuration to an "expanded" post-deployment configuration. In the illustrated embodiment, the band element 212 comprises a plurality of uniformly shaped closed, interconnecting cells 214, and a plurality of connector elements 216 extending between and interconnecting longitudinally spaced portions of the band 212 over its tubular length C.

As set forth in Applicant's U.S. Pat. No. 9,044,319, the cells 214 can comprise various shapes, such as the diamond shape shown in FIGS. 4A and 4B.

Referring now to FIGS. 5A, 5B, 6A and 6B, there is shown another embodiment of an annular ring of the invention (denoted "220"), which is also disclosed and discussed in detail in Applicant's U.S. Pat. No. 9,044,319.

As illustrated in FIGS. 5A, 5B, 6A and 6B, to provide a "contracted" pre-deployment configuration and facilitate transition therefrom to a desired "expanded" post-deployment configuration, the annular ring 220 preferably comprises a discontinuous band 222, where one end 224 of the annular ring 220 over-laps the other end 226 of the annular ring 220.

As further illustrated in FIGS. 5A, 5B, 6A and 6B, the discontinuous band 222 comprises engagement holes 228a, 228b, 228c, 228d on an edge region (i.e., proximal edge region 231a or distal edge region 231b) of the band 222, which, as discussed in detail below, are sized and configured to receive and engage the proximal ends of the cardiovascular structure engagement members of the invention, e.g., cardiovascular structure engagement members 206a, 206b, 206c shown in FIGS. 2A and 2B.

In some embodiments, the annular ring 220 comprises a multiple discontinuous band laminate structure, e.g., two band structures.

Referring now to FIGS. 7A, 7B, 7C and 7D, there is shown another embodiment of an annular ring of the invention (denoted "250"), which is similarly adapted to transition from a "contracted" pre-deployment configuration to an "expanded" post-deployment configuration.

Figure 7A:
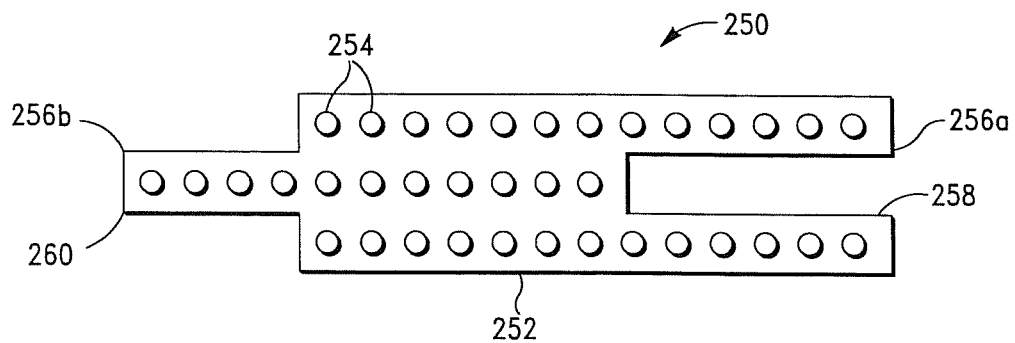
FIG. 7A is a top plan view of another embodiment of a support structure annular ring, in accordance with the invention.
Figure 7B:
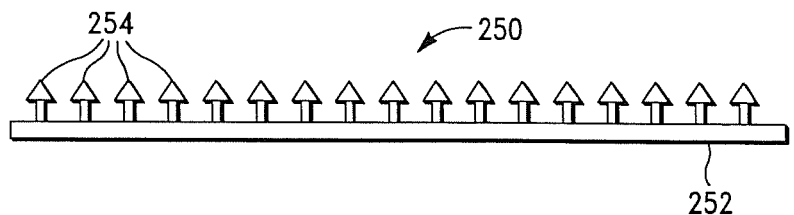
FIG. 7B is a front plan view of the annular ring shown in FIG. 7A, in accordance with the invention.

As illustrated in FIGS. 7A and 7B, the annular ring 250, which is also disclosed and discussed in detail in Applicant's U.S. Pat. No. 9,044,319, comprises a microneedle anchoring mechanism having a base 252 and a plurality of biodegradable microneedles or barbs 254 that are adapted to position and secure the annular ring members and, hence, prosthetic valves associated therewith to a cardiovascular structure and, hence, the cardiovascular tissue thereof and maintain engagement thereto for an enhanced support time period.

As also illustrated in FIGS. 7A and 7B, to facilitate transitioning from a pre-deployment configuration, as shown in FIG. 7A, to a post-deployment configuration, as shown in FIG. 7B, one end 256a of the microneedle annular ring 250 preferably includes an elongated slot 258 that is designed and configured to receive the base projection 260 on the opposing end 256b of the base 252.

Figures 7C, 7D:
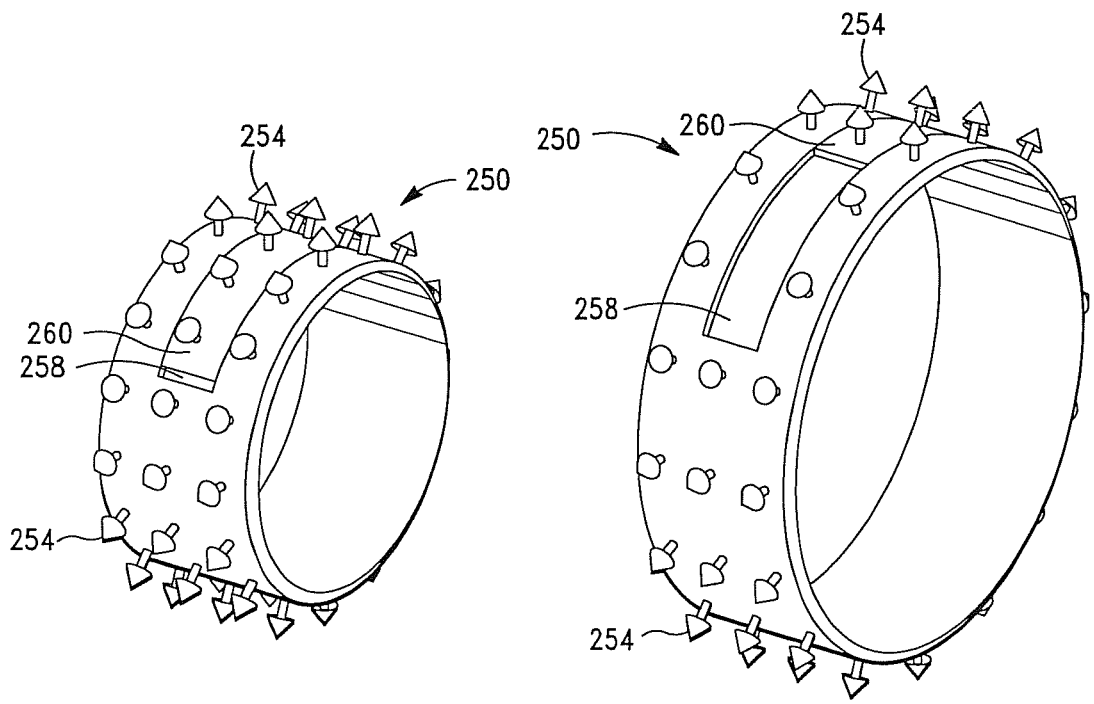
FIG. 7C is a perspective view of the annular ring shown in FIGS. 7A and 7B in a pre-deployment configuration, in accordance with the invention.
FIG. 7D is a perspective view of the annular ring shown in FIGS. 7A and 7B in a post-deployment configuration, in accordance with the invention.

As illustrated in FIG. 7C, when the microneedle annular ring 250 is in a pre-deployment configuration, the elongated slot 258 slidably receives the base projection 260 therein. As illustrated in FIG. 7D, when the microneedle annular ring 250 transitions to a post-deployment configuration, the base projection 260 transitions (or moves) within the elongated slot 258, wherein a larger diameter post-deployment configuration is provided.

According to the invention, the annular ring members can also comprise any pre-deployment and post-deployment shape, size and configuration.

Preferably, the annular rings of the invention comprise a pre-deployment or pre-implantation diameter in the range of 0.33-8 mm (1-24 French). In some embodiments of the invention, the annular rings of the invention comprise a pre-deployment diameter in the range of 1.67-6.67 mm (5-20 French).

Preferably, the annular ring members also comprise a post-deployment or post-implantation diameter in the range of 5-66.67 mm (15-200 French). In some embodiments, the annular ring members comprise a post-deployment diameter in the range of 20-40 mm (60-120 French).

According to the invention, the annular rings of the invention can also comprise various biocompatible materials.

As indicated above, in some embodiments of the invention, the annular rings comprise a biocompatible metal.

According to the invention, suitable biocompatible metals comprise, without limitation, Nitinol®, titanium, stainless steel and magnesium.

In some embodiments of the invention, the annular rings comprise one of the aforementioned polymeric compositions.

In some embodiments of the invention, the polymeric compositions comprise at least one biodegradable polymer.

According to the invention, suitable biodegradable polymers, include without limitation, polyurethane urea (Artelon®), poly(ε-caprolactone) (PCL), poly(glycerol sebacate) (PGS) and poly(glycerol sebacate) acrylate (PGSA).

Additional suitable biodegradable polymers are disclosed in Applicant's U.S. application Ser. No. 16/418,063 and U.S. Pat. Nos. 9,149,496 and 9,694,104.

In some embodiments of the invention, the polymeric compositions comprise at least one non-biodegradable polymer.

According to the invention, suitable non-biodegradable polymers, include without limitation, polytetrafluoroethylene (Teflon®) and polyethylene terephthalate (Dacron®).

Additional suitable non-biodegradable polymers are disclosed in Applicant's U.S. application Ser. Nos. 16/418,063.

In some embodiments of the invention, the annular rings comprise one of the aforementioned ECM compositions.

In some embodiments, the noted compositions comprise at least one of the aforementioned biologically active agents and/or pharmacologically active agents.

In some embodiments, the annular ring members comprise a physiological sensor system, such as the physiological sensor systems disclosed in Applicant's Co-Pending U.S. application Ser. Nos. 16/369,174 and 16/418,063, which are incorporated by reference herein in their entirety.

In some embodiments, the annular ring members further comprise at least one coating that is disposed over at least a portion of the annular ring members' outer surface.

According to the invention, suitable annular ring coatings are set forth in Applicant's U.S. Pat. Nos. 9,533,072 and 10,143,778, which are incorporated by reference herein in their entirety.

As set forth in Applicant's U.S. Pat. Nos. 9,533,072 and 10,143,778, the annular ring coatings can thus comprise, without limitation, PGS and compositions comprising ECM and PGS.

In some embodiments of the invention, the annular ring coatings comprise one of the aforementioned polymeric compositions.

In some embodiments of the invention, the annular ring coatings comprise one of the aforementioned ECM compositions.

In some embodiments, the noted coating compositions comprise at least one of the aforementioned biologically active agents and/or pharmacologically active agents.

According to the invention, the coatings can be applied to the annular rings using any conventional method, including, without limitation, dip coating, spin coating, spray coating, etc. The coatings can also comprise at least one sheet of material that is applied to at least a portion of the outer surface of an annular ring.

In some embodiments, the annular ring coating is adapted to facilitate adherence and, hence, engagement of an annular ring and, hence, support structure to a prosthetic valve.

Thus, when an annular ring and, hence, support structure is disposed between sheet layers, as shown in FIGS. 2A and 2B (and discussed in detail below), the annular ring coating facilitates adherence of the annular ring and, hence, support structure to the sheet layers, thereby substantially preventing, more preferably, eliminating delamination of the sheet layers proximate the annular ring.

In some embodiments, the annular ring coating comprises an adhesive composition. According to the invention, the adhesive composition can comprise any conventional biocompatible adhesive composition, such as a fibrin-based composition or a collagen-based composition.

In some embodiments, the adhesive composition comprises at least one of the aforementioned biologically active agents and/or pharmacological agents.

In some embodiments, the annular ring comprises at least one micro-structured surface having a coating disposed thereon. Preferably, the micro-structured surface is configured to increase the surface area and, thereby, increase at least the adhesion, friction, hydrophilicity and/or hydrophobicity of the coating.

Suitable micro-structured surfaces are disclosed in U.S. application Ser. Nos. 14/953,561 and 14/802,632, which are incorporated by reference in their entirety.

Cardiovascular Structure Engagement Members

As indicated above, the support structures of the invention comprise at least one, more preferably, a plurality of elongated cardiovascular structure engagement members, which are in communication with and extend outwardly from the distal end of the annular ring.

According to the invention, the cardiovascular structure engagement members can comprise various configurations and structures, including, without limitation, single fiber and/or filament structures, such as metal wire and polymer fibers and/or filaments, solid tubular structures, multiple fiber and filament structures, such as braided wire structures, and laminated structures, such as flat sheet structures.

The elongated cardiovascular structure engagement members are also preferably flexible.

In some embodiments of the invention, the cardiovascular structure engagement members are also stretchable linearly.

According to the invention, the cardiovascular structure engagement members of the invention can comprise any length; provided, when the cardiovascular structure engagement members are engaged to a support structure annular ring and the support structure is operatively positioned in or on a prosthetic valve, the distal end of the cardiovascular structure engagement members extend out of the distal end of the valve.

In a preferred embodiment of the invention, the cardiovascular structure engagement members of the invention have a minimal strength in the range of at least approximately 60-500 MPa.

According to the invention, the cardiovascular structure engagement members of the invention can similarly comprise various biocompatible materials.

In some embodiments of the invention, the cardiovascular structure engagement members similarly comprise a biocompatible metal.

According to the invention, suitable biocompatible metals similarly comprise, without limitation, Nitinol®, titanium, stainless steel and magnesium.

In a preferred embodiment of the invention, the cardiovascular structure engagement members comprise Dyneema®, which, as indicated above, is a high strength, ultra-high molecular weight polyethylene (UHMwPE).

Indeed, Dyneema®, when in fiber form, is considered by many to be the world's strongest fiber and the only high molecular weight polyethylene (HMPE) fiber that is highly resistant to bending and creep fatigue.

Dyneema® is typically subjected to a unique gel spinning process, which alters the molecular alignment, whereby the processed HMPE exhibits higher crystallization and lower density when compared to unprocessed polyethylene. The HMPE also exhibits longer molecular chains that more effectively transfer physical load to the polymer backbone of the HMPE.

As a result, the HMPE and, hence, Dyneema® fibers generally exhibit a yield strength of at least 2.4 GPa (350,000 psi) and a minimum density of at least 0.97 g/cm³. Dyneema fibers thus comprise a strength-to-weight ratio that far surpasses the strength-to-weight ratio of fibers that comprise other conventional polymers and biocompatible metals.

Dyneema® is also non-immunogenic and, thus, substantially limits the acute inflammatory responses typically associated with other conventional polymers, such as polyamide-based polymers.

Thus, according to the invention, when a cardiovascular structure engagement member of the invention comprises Dyneema®, the Dyneema® cardiovascular structure engagement members significantly enhance the structural integrity of the support structure and, thereby, prosthetic valve employing same.

According to the invention, the cardiovascular structure engagement members can also comprise an interwoven blend of various filaments, fibers and/or wires comprising the aforementioned cardiovascular structure engagement member materials, such as, by example, a blend of Dyneema® and Nitinol® filaments.

In some embodiments of the invention, the cardiovascular structure engagement members comprise one of the aforementioned polymeric compositions.

In some embodiments, the noted compositions comprise at least one of the aforementioned biologically active agents and/or pharmacologically active agents.

In some embodiments, the cardiovascular structure engagement members similarly comprise one of the aforementioned annular ring coatings.

Figure 8:
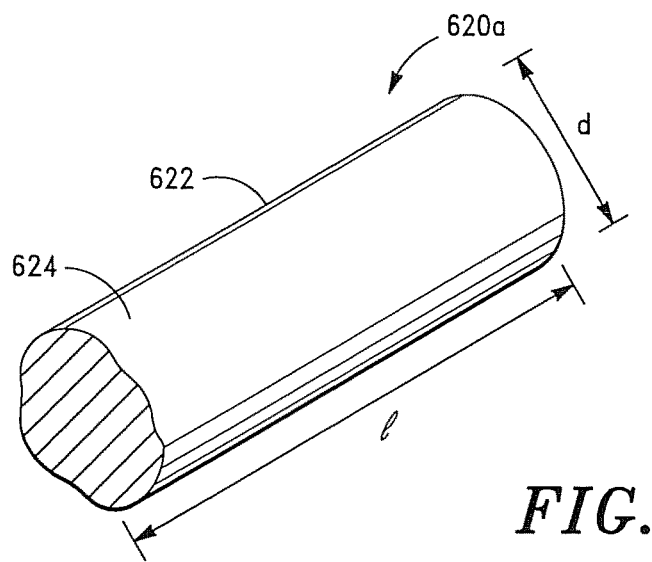
FIG. 8 is a partial perspective, partial sectional view of one embodiment of a cardiovascular structure engagement member, in accordance with the invention.

Referring now to FIG. 8, there is shown one embodiment of an elongated cardiovascular structure engagement member of the invention (denoted "620a"). As illustrated in FIG. 8, the elongated cardiovascular structure engagement member 620a comprises an elongated single filament member or structure 622 having a top surface 624.

According to the invention, the single filament structure 622 can comprise a metal wire, metal or polymer filament, single polymer fiber, or like structure.

As indicated above, the single filament structure 622 and, hence, cardiovascular structure engagement member 620a can comprise any length "$\ell$"; provided, when the cardiovascular structure engagement member 620a is engaged to a support structure annular ring and the support structure is operatively positioned in or on a prosthetic valve, the distal end of the cardiovascular structure engagement member 620a extends out of the distal end of the valve.

According to the invention, the single filament structure 622 and, hence, cardiovascular structure engagement member 620a, can also comprise any suitable diameter "d"; provided, the cardiovascular 60-250 MPa.

Figure 9:
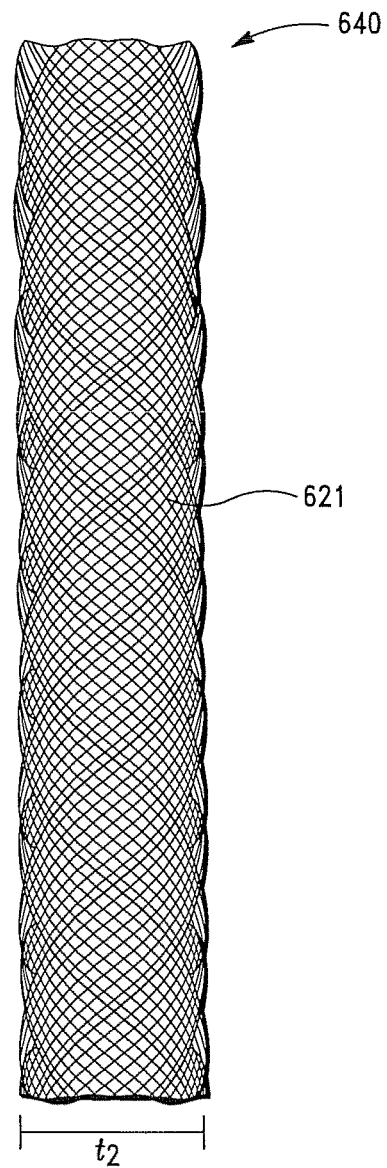
FIG. 9 is a partial front plan view of another embodiment of a cardiovascular structure engagement member, in accordance with the invention.

Referring now to FIG. 9, there is shown another embodiment of an elongated cardiovascular structure engagement member of the invention (denoted "640"). As illustrated in FIG. 9, the elongated cardiovascular structure engagement member 640 similarly comprises an elongated filament member or structure 621. However, in this embodiment, the filament structure 621 comprises a braided structure, i.e., a plurality of interwoven filaments, fibers and/or wires.

Figure 10A:
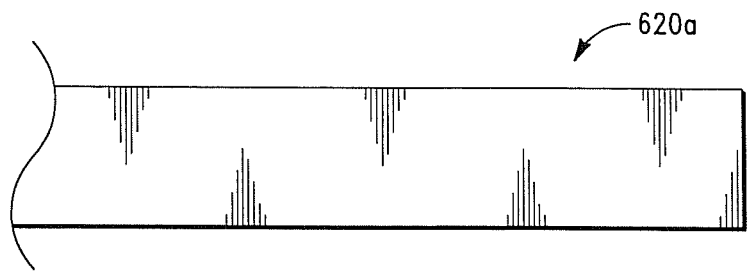
FIG. 10A is a partial front plan view of the cardiovascular structure engagement member shown in FIG. 8, illustrating one embodiment of the distal end of the member, in accordance with the invention.
Figure 10B:
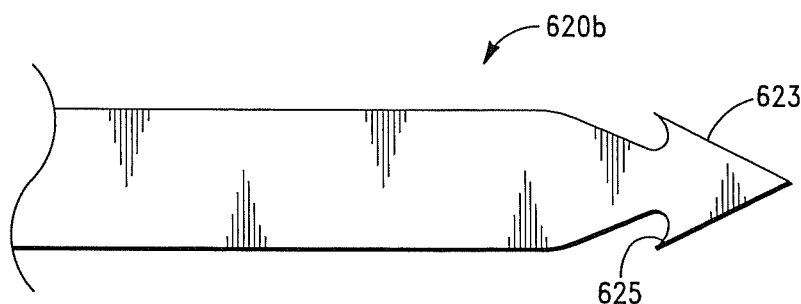
FIGS. 10B and 10C are partial front plan views of the cardiovascular structure engagement member shown in FIG. 8, illustrating embodiments of tissue engaging distal ends of the member, in accordance with the invention.
Figure 10C:
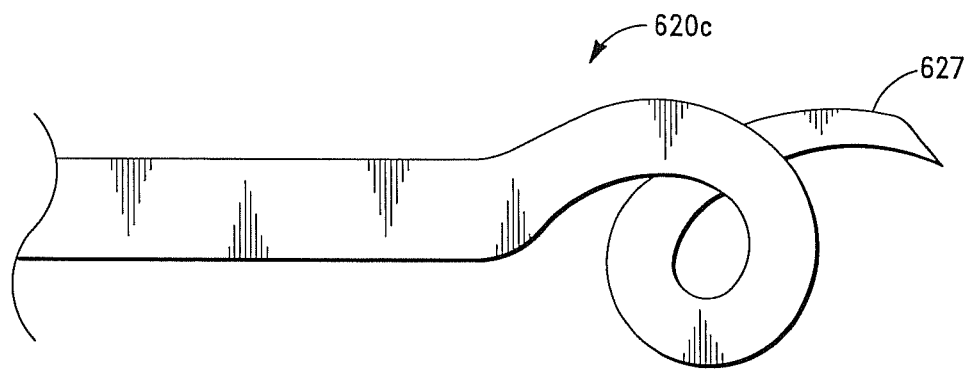

Referring now to FIGS. 10A, 10B and 10C, according to the invention, the distal ends of the cardiovascular structure engagement members of the invention can comprise various configurations.

In some embodiments of the invention, the distal ends of the cardiovascular structure engagement members comprise a tissue engaging configuration.

Referring now to FIG. 10B, there is shown one embodiment of a tissue engaging distal end 623 of a cardiovascular structure engagement member (denoted "620b"). As illustrated in FIG. 10B, the tissue engaging distal end 623 comprises a pointed conical structure with a rearward facing barb 625.

Retelling now to FIG. 10C, there is shown another embodiment of a tissue engaging distal end 627 of a cardiovascular structure engagement member (denoted "620c"). As illustrated in FIG. 10C, the tissue engaging distal end 627 comprises a pointed screw structure.

It should, however, be understood that the tissue engaging ends illustrated in FIGS. 10B and 10C are not limiting. Indeed, according to the invention, various addition cardiovascular structure engagement member distal end configurations having conventional configurations that are adapted to pierce and engage tissue can be employed within the scope of the invention.

According to the invention, the distal ends of the cardiovascular structure engagement members can also comprise a blunt end, such as illustrated in FIG. 10A, to facilitate engagement to a support structure anchor (discussed in detail below).

Referring now to FIGS. 11-15, several embodiments of complete support structures of the invention will be described in detail.

Figure 11:
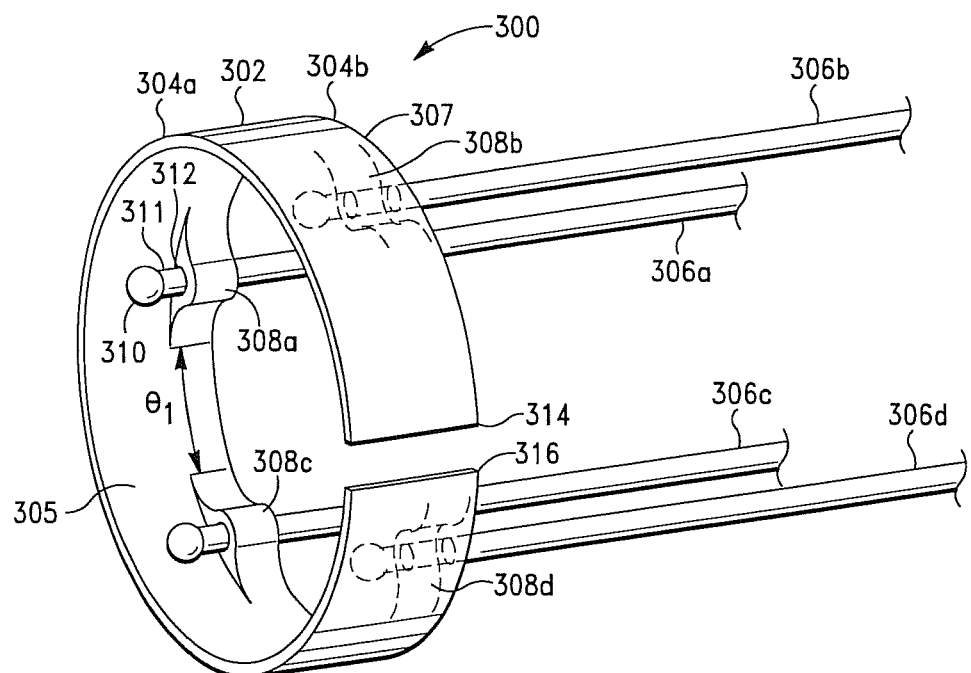
FIGS. 11 through 15 are perspective views of various embodiments of support structures, in accordance with the invention.

Referring first to FIG. 11, there is shown there is shown one embodiment of a support structure of the invention (denoted "300"). As illustrated in FIG. 11, the support structure 300 comprises an annular ring 302 and a plurality of cardiovascular structure engagement members 306a, 306b, 306c, 306d comprising proximal ends 311.

The annular ring 302, in this embodiment, comprises a discontinuous band member 307 comprising ends 314 and 316, proximal and distal end regions 304a and 304b, an inner surface 305 and cardiovascular structure engagement member connection means 308a, 308b, 308c, 308d.

In a preferred embodiment of the invention, the support structure 300 is similarly configured to transition from a "contracted" pre-deployment configuration to an "expanded" post-deployment configuration. To provide the "contracted" pre-deployment configuration and facilitate transition therefrom to a desired "expanded" post-deployment configuration, the band member 307 is designed and configured to allow end 314 to over-lap end 316 proximate the inner surface 305 of the band member 307 without end 316 being obstructed by the cardiovascular structure engagement member connection means discussed below.

As further illustrated in FIG. 11, the cardiovascular structure engagement member connection means 308a, 308b, 308c, 308d comprise raised annular ring regions that are disposed on the inner surface 305 of the annular ring 302 at defined circumferential distance intervals "θ₁". Each of the raised annular ring regions 308a, 308b, 308c, 308d includes a lumen 312 that is sized and configured to receive the proximal end 311 of a cardiovascular structure engagement member, e.g., cardiovascular structure engagement member 306a, therein.

In a preferred embodiment, each of the lumens 312 is also sized and configured to allow a cardiovascular structure engagement member, when disposed therein, to translate slidably and rotatably.

According to the invention, the raised annular ring regions 308a, 308b, 308c, 308d can be disposed at any defined circumferential distance interval θ₁ on the inner surface 305 of the annular ring 302. As illustrated in FIG. 11, in a preferred embodiment, the raised annular ring regions 308a, 308b, 308c, 308d are spaced at an equidistant circumferential distance intervals.

As further illustrated in FIG. 11, each of the cardiovascular structure engagement members 306a, 306b, 306c, 306d preferably includes retention means 310 that is disposed on the proximal end 311 thereof, which is sized and configured to retain the proximal ends 311 of cardiovascular structure engagement members 306a, 306b, 306c, 306d in the raised annular ring regions 308a, 308b, 308c, 308d lumens 312, while allowing the cardiovascular structure engagement members 306a, 306b, 306c, 306d to slidably and rotatably translate therein.

According to the invention, the retention means 310 can comprise any configuration. In a preferred embodiment, the retention means 310 comprises a ball shape, such as illustrated in FIG. 11.

Figure 12:
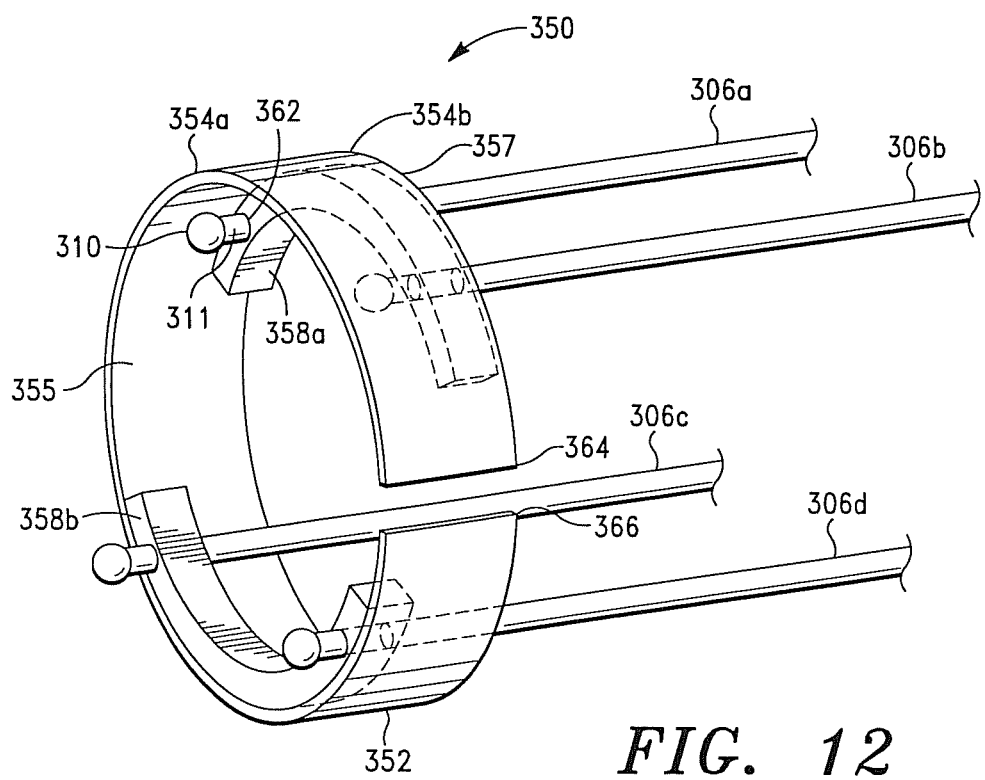

Referring now to FIG. 12, there is shown another embodiment of a support structure of the invention (denoted "350"). As illustrated in FIG. 12, the support structure 350 similarly comprises an annular ring 352 and cardiovascular structure engagement members 306a, 306b, 306c, 306.

As further illustrated in FIG. 12, the annular ring 352 similarly comprises a discontinuous band member 357 having ends 364 and 366, proximal and distal end regions 354a and 354b, an inner surface 355.

In a preferred embodiment of the invention, the support structure 350 is similarly configured to transition from a "contracted" pre-deployment configuration to an "expanded" post-deployment configuration. To provide the "contracted" pre-deployment configuration and facilitate transition therefrom to a desired "expanded" post-deployment configuration, the band member 357 is designed and configured to allow end 364 to over-lap end 366 proximate the inner surface 355 of the band member 357 without end 366 being obstructed by the shoulder members discussed below.

In this embodiment, the annular ring 352 further comprises discontinuous shoulder members 358a, 358b; shoulder member 358a being disposed on (i.e., projects from) the inner surface 355 of the annular ring member 352 proximate the distal end region 354b and shoulder member 358b being disposed on (i.e., projects from) the inner surface 355 of the annular ring member 352 proximate the proximal end region 354a.

According to the invention, the raised shoulder members 358a, 358b can comprise any shape and size; provided, the shape and size of the shoulder members 358a, 358b allows the annular ring 352 to contract to a pre-deployment configuration and transition therefrom to an expanded post-deployment configuration.

As further illustrated in FIG. 12, each of the shoulder members 358a, 358b similarly comprise lumens 362 that are configured to receive cardiovascular structure engagement members 306a, 306b, 306c, 306d therein and allow the cardiovascular structure engagement members 306a, 306b, 306c, 306d to slidably and rotatably translate therein.

Figure 13:
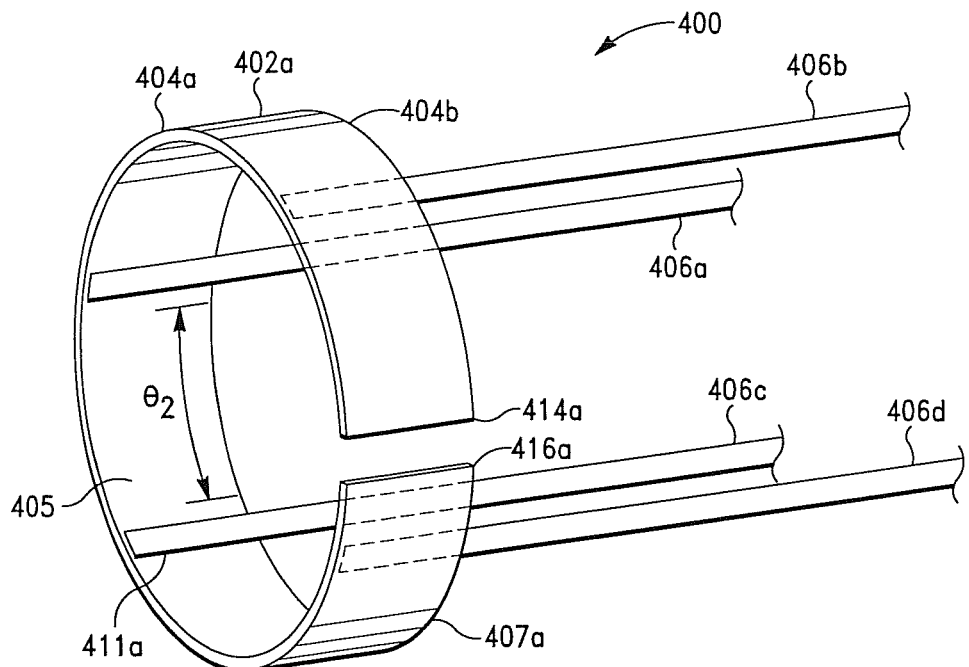

Referring now to FIG. 13, there is shown another embodiment of a support structure of the invention (denoted "400"). As illustrated in FIG. 13, the support structure 400 similarly comprises an annular ring 402a and cardiovascular structure engagement members 406a, 406b, 406c, 406d having proximal ends 411a. The annular ring member 402a similarly comprises a discontinuous band member 407a having ends 414a and 416a, proximal and distal end regions 404a and 404b and an inner surface 405.

As further illustrated in FIG. 13, the proximal ends 411a of the cardiovascular structure engagement members 406a, 406b, 406c, 406d are in communication with, more preferably, secured to the inner surface 405 of the annular ring 402a.

According to the invention, the proximal ends 411a of the cardiovascular structure engagement members 406a, 406b, 406c, 406d can be secured to the inner surface 405 using any conventional method.

According to the invention, the cardiovascular structure engagement members 406a, 406b, 406c, 406d can be disposed on the inner surface 405 of the annular ring 402a at any defined circumferential distance interval "θ₂".

Figure 14:
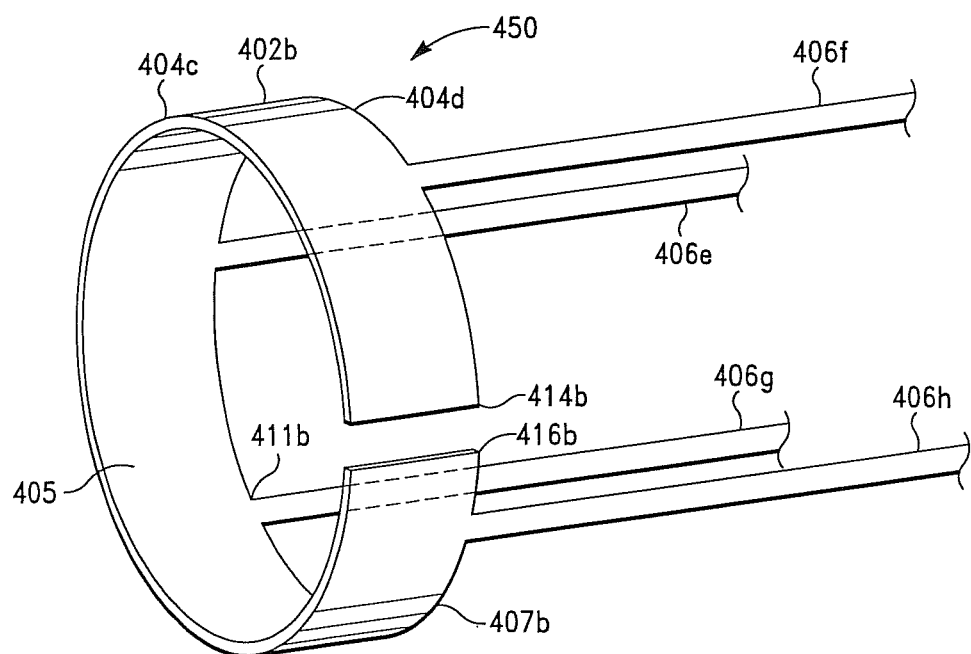

Referring now to FIG. 14, there is shown another embodiment of a support structure of the invention (denoted "450"). As illustrated in FIG. 14, the support structure 450 similarly comprises an annular ring member 402b, i.e., discontinuous band member 407b, and a plurality of cardiovascular structure engagement members 406e, 406f, 406g, 406h.

As further illustrated in FIG. 14, in this embodiment, the cardiovascular structure engagement members 406e, 406f, 406g, 406h are integral with the annular ring member 402b and extend outwardly from the distal end region 404d of the annular ring 402.

Figure 15:
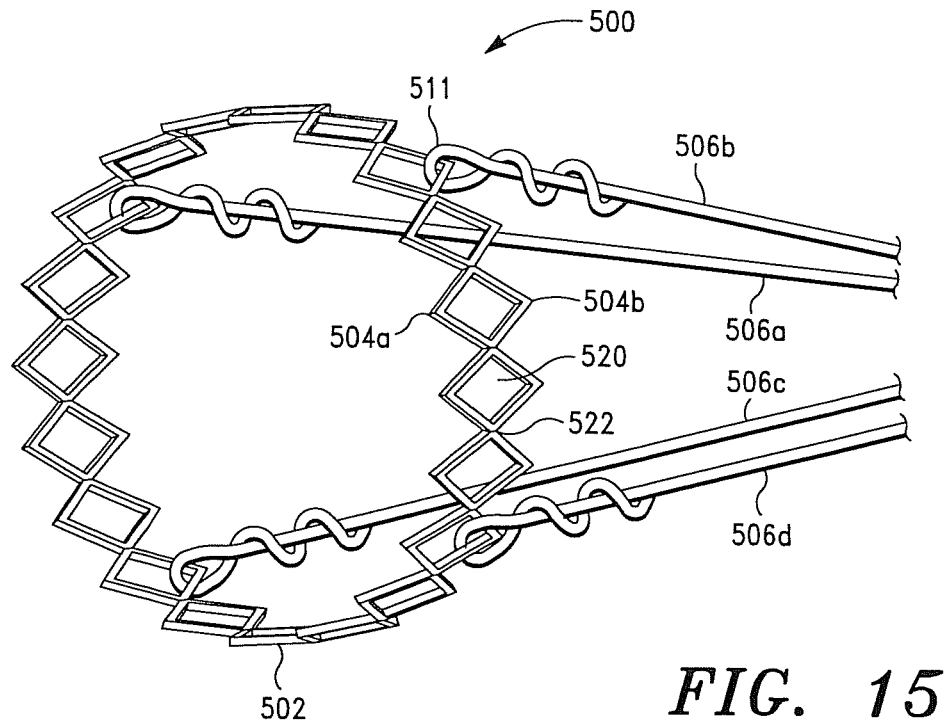

Referring now to FIG. 15, there is shown another embodiment of a support structure of the invention (denoted "500"). As illustrated in FIG. 15, the support structure 500 comprises a continuous, helically arranged band element 502, such as shown in FIG. 4A. The band element 502 preferably comprises a plurality of uniformly shaped interconnecting cells 520, and a plurality of connector elements 522 extending between and interconnecting longitudinally spaced portions of the band 502.

As further illustrated in FIG. 15, the support structure 500 further comprises cardiovascular structure engagement members 506a, 506b, 506c, 506d that are connected to, e.g., tied or wound, cells 520 (on the proximal 504a or distal end 504b, preferably, the distal end 504b).

In a preferred embodiment, the support structures of the invention further comprise a tissue anchor that is designed and configured (i) to receive and retain the cardiovascular structure engagement members and (ii) engage tissue of a cardiovascular structure and secure the cardiovascular structure engagement members and, thereby, prosthetic valve associated therewith to the cardiovascular structure and maintain contact therewith for a pre-determined period of time.

According to the invention, the tissue anchor can comprise any shape and size; provided, the shape and size accommodate entry into and through biological tissue and tissue structures.

In some embodiments, the tissue anchor comprises a conventional leadscrew, e.g., a Nitinol worm screw. In some embodiments, the anchor members comprise a conventional tined leadscrew. In some embodiments, the anchor members comprise a tined conical member.

In some embodiments, the tissue anchor comprises a conventional suture anchor device, such as the Tornier Insite® suture anchor.

According to the invention, the tissue anchor can comprise one of the aforementioned metals and compositions; particularly, one of the aforementioned polymeric compositions.

According to the invention, the tissue anchor can also comprise one of the aforementioned annular ring coatings.

Figure 16:
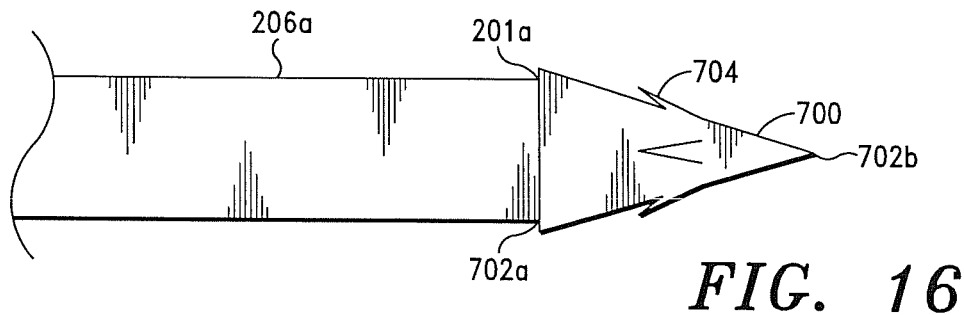
FIG. 16 is a side plan view of one embodiment of a tissue anchor, in accordance with the invention.

Referring now to FIG. 16, there is shown one embodiment of a tissue anchor of the invention (denoted "700"). As illustrated in FIG. 16, the anchor 700 comprises a piercing distal end 702b, a proximal end 702a and a plurality of barbs 704.

As further illustrated in FIG. 16, the anchor 700 is also configured to receive and retain the distal end 201a of a cardiovascular structure engagement member, such as cardiovascular structure engagement member 206a therein.

According to the invention, the distal end 201a of the cardiovascular structure engagement member 206a can be secured to the anchor member 700 via any conventional securing method.

Figure 17:
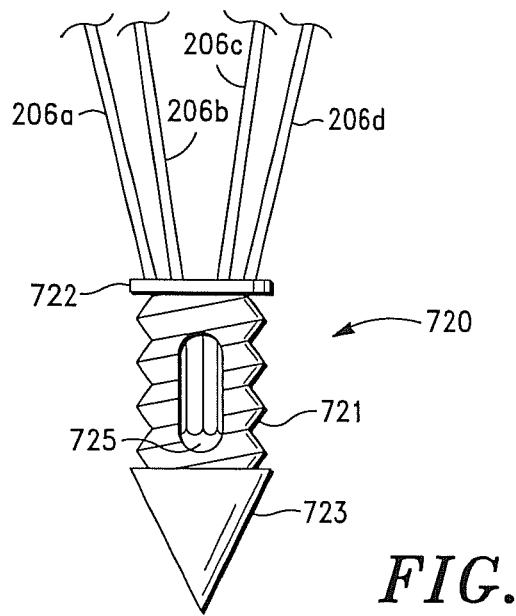
FIG. 17 is a side view of another embodiment of a tissue anchor, in accordance with the invention.

Referring now to FIG. 17, there is shown another embodiment of a tissue anchor of the invention (denoted "720"). As illustrated in FIG. 17, the anchor 720 comprises a spiral cylindrical member 721 having a distal piercing head 723, a proximal base end 722 and an internal region 725.

As further illustrated in FIG. 17, the anchor 720 similarly comprises a threading member or eyelet (not shown) disposed in the internal region 725 that is configured to receive and secure the distal ends of cardiovascular structure engagement members, such as cardiovascular structure engagement members 206a, 206b, 206c, 206d thereto, i.e., threaded through and tied thereto.

Figure 18:
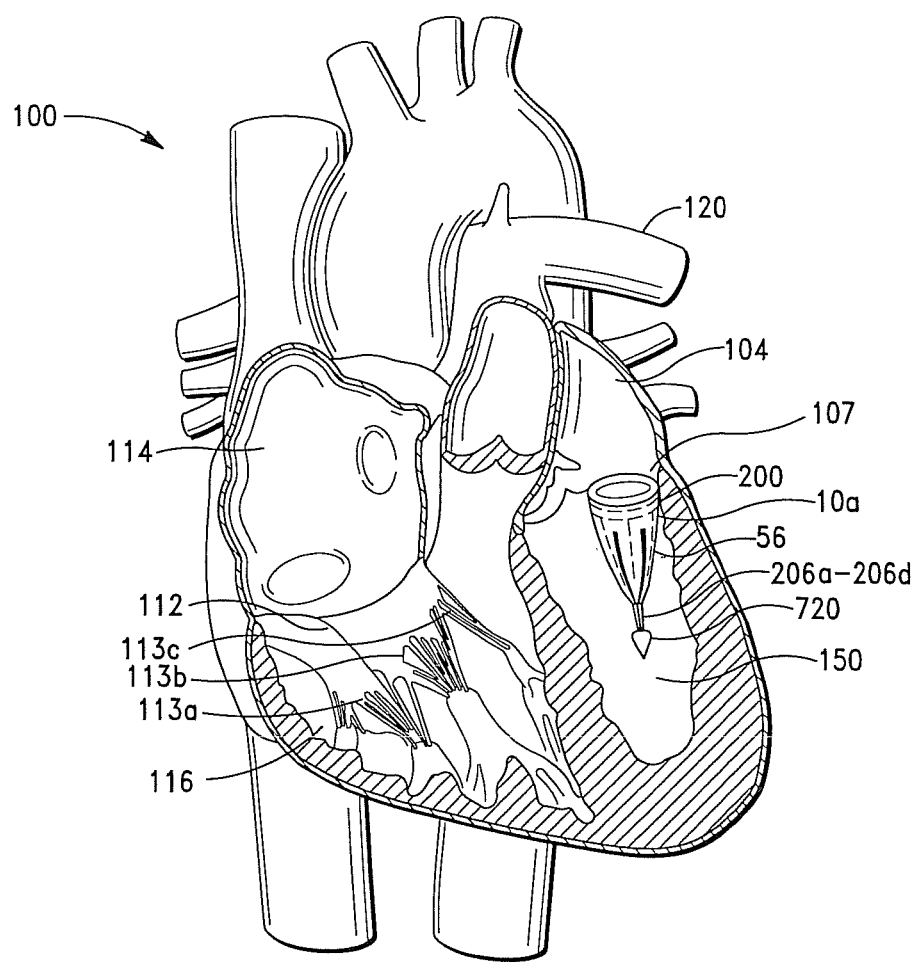
FIG. 18 is an illustration of the prosthetic valve shown in FIG. 2A having one embodiment of a support structure secured to the mitral valve annulus region and ventricular wall, in accordance with the invention.

Referring now to FIG. 18, placement of prosthetic valve 10a having a support structure of the invention in a mitral valve region will now be described in detail.

After the mitral valve annulus region 107 is prepared and, if elected, the mitral valve 102 and chordae tendineae 103a, 103b are removed, the prosthetic valve 10a is disposed proximate the mitral valve annulus region 107. The proximal end 52 of the prosthetic valve 10a is then secured to the mitral valve annulus.

As illustrated in FIG. 18, in accordance with one embodiment of the invention, the tissue anchor 720 (if employed) having the distal ends of cardiovascular structure engagement members 206a, 206b, 206c, 206d secured thereto is then driven into and secured to, i.e., engaged with, the ventricular wall 150.

In a preferred embodiment, the anchor 720 is driven into and secured to the ventricular wall 150 in a manner that provides the cardiovascular structure engagement members 206a, 206b, 206c, 206d of the support structure 200 with sufficient length to allow prosthetic valve 10a to function as intended, i.e., close when fluid flow through the valve exhibits a negative flow pressure and open when fluid flow through the valve exhibits a positive flow pressure.

Figure 19:
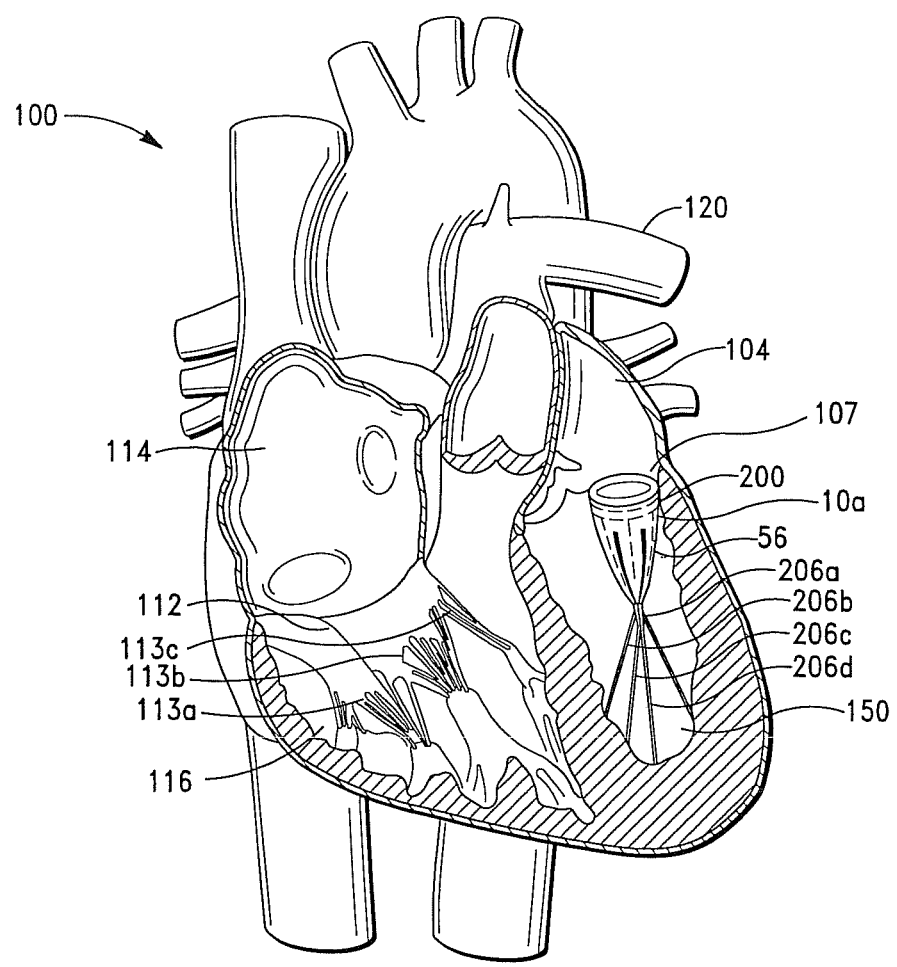
FIG. 19 is an illustration of the prosthetic valve shown in FIG. 2A having another embodiment of a support structure secured to the mitral valve annulus region and ventricular wall, in accordance with the invention.

Referring now to FIG. 19, there is shown another illustration of prosthetic valve 10a having another embodiment of a support structure of the invention placed in a mitral valve region.

After the mitral valve annulus region 107 is similarly prepared and, if elected, the mitral valve 102 and chordae tendineae 103a, 103b are removed, the valve 10a is disposed proximate the mitral valve annulus region 107. The proximal end 52 of the prosthetic valve 10a is then secured to the mitral valve annulus.

As illustrated in FIG. 19, in accordance with one embodiment of the invention, each of the cardiovascular structure engagement members 206a, 206b, 206c, 206d of the support structure comprise a tissue engaging end, such as shown in FIGS. 10B and 10C, which are then driven into and secured to, i.e., engaged with, the ventricular wall 150.

According to the invention, the distal tissue engaging ends of the cardiovascular structure engagement members 206a, 206b, 206c, 206d can be secured to various regions on interior and external ventricular wall regions.

Preferably, the distal tissue engaging ends of the cardiovascular structure engagement members 206a, 206b, 206c, 206d are secured to an interior region of the ventricular wall 150 in a manner that similarly provides the cardiovascular structure engagement members 206a, 206b, 206c, 206d of the support structure 200 with sufficient length to allow prosthetic valve 10a to function as intended, i.e., close when fluid flow through the valve exhibits a negative flow pressure and open when fluid flow through the valve exhibits a positive flow pressure.

Figure 20:
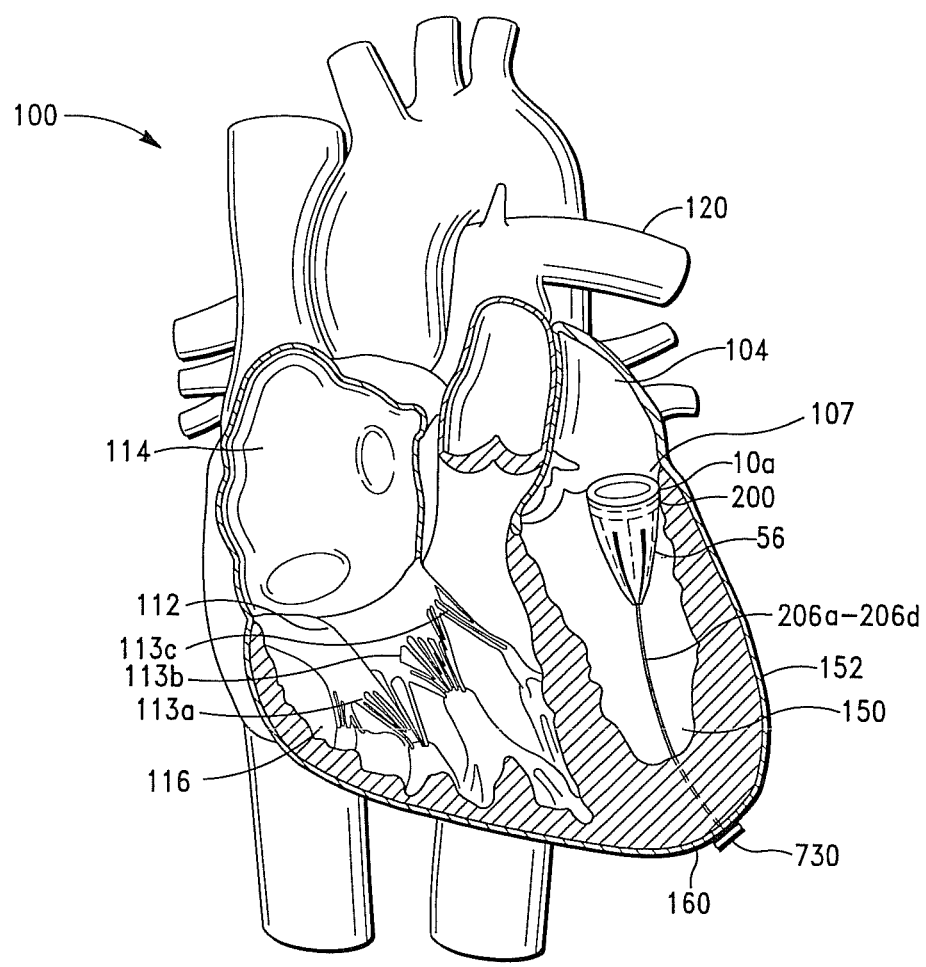
FIG. 20 is an illustration of the prosthetic valve shown in FIG. 2A secured to the mitral valve annulus region and ventricular wall using an external anchor member, in accordance with the invention.

Referring now to FIG. 20, in some embodiments of the invention, the distal ends of the cardiovascular structure engagement members 206a, 206b, 206c, 206d are threaded into and through the ventricular wall 150 and secured to an external ventricular wall region via an external anchor 730.

In some embodiments, the external anchor 730 abuts the apex 160 of heart 100.

In some embodiments, the external anchor member 730 comprises a conventional surgical pledget.

According to the invention, the distal ends of the cardiovascular structure engagement members 206a, 206b, 206c, 206d can also be threaded into and through (and, hence, engaged to) one or more desired papillary muscles.

According to the invention, the prosthetic valves of the invention, i.e., prosthetic valves 10a-10d, are designed and configured to be deployed in a valve annulus region using any conventional transcatheter valve implantation system or method.

According to the invention, the prosthetic valves of the invention, i.e., prosthetic valves 10a-10d, can deployed in a valve annulus region via the systems and methods disclosed in Applicant's Co-pending U.S. application Ser. Nos. 16/193,669, 16/238,730 and 16/553,570, which are incorporated by reference herein in their entirety.

According to the invention, the support structures can be incorporated into any of the prosthetic valves disclosed in Applicant's U.S. Pat. Nos. 7,998,196, 8,696,744, 9,241,789, 8,790,397, 8,845,719, 9,226,821, 9,308,084, 9,907,649, 10,188,509, 10,188,510, 10,052,409, and U.S. application Ser. Nos. 16/129,968, 15/877,629, 16/440,504 and 16/553, 499.

As will readily be appreciated by one having ordinary skill in the art, the present invention provides numerous advantages compared to prior art prosthetic valves. Among the advantages are the following:

The provision of improved methods for securely attaching prosthetic valves to cardiovascular structures and/or tissue;

The provision of prosthetic valves having means for secure, reliable, and consistently highly effective attachment to cardiovascular structures and/or tissue;

The provision of improved prosthetic valves and methods for attaching same to cardiovascular structures and/or tissue that maintain or enhance the structural integrity of the valve when subjected to cardiac cycle induced stress;

The provision of improved prosthetic valves and methods for attaching same to cardiovascular structures and/or tissue that preserve the structural integrity of the cardiovascular structure(s) when attached thereto;

The provision of prosthetic valves that induce modulated healing, including host tissue proliferation, bioremodeling and regeneration of new tissue and tissue structures with site-specific structural and functional properties;

The provision of prosthetic valves that induce adaptive regeneration;

The provision of prosthetic valves that are capable of administering a pharmacological agent to host tissue and, thereby produce a desired biological and/or therapeutic effect;

The provision prosthetic valves that can be implanted without removal of the native AV valve;

The provision of prosthetic valves that can be implanted without a cardiopulmonary bypass apparatus;

The provision prosthetic valves that can be positioned proximate a valve annulus transvascularly; and The provision prosthetic valves that can be positioned proximate a valve annulus transapically.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A prosthetic valve for modulating fluid flow through an atrioventricular (AV) valve annulus region during cardiac cycles of a heart, said fluid flow exhibiting a plurality of fluid pressures during said cardiac cycles, said prosthetic valve comprising:

a continuous conical shaped biological tissue member and a support structure, said biological tissue member comprising an adaptive tissue regeneration system adapted to induce modulated healing of cardiovascular tissue of said AV valve annulus region concomitantly with stress-induced hypertrophy of said biological tissue member when said biological tissue member is subjected to cardiac cycle induced physical stimuli, said modulated healing of said cardiovascular tissue comprising inflammation modulation of said cardiovascular tissue and induced neovascularization, remodeling of said cardiovascular tissue and regeneration of new cardiovascular tissue and tissue structures with site-specific structural and functional properties, said stress-induced hypertrophy of said biological tissue member comprising adaptive remodeling of said biological tissue member, wherein said biological tissue member forms functioning valve structures that are similar to native valve structures, said adaptive tissue regeneration system of said biological tissue member comprising a material component and a physical structure component, said material component comprising mammalian-based tissue derived from a mammalian tissue source, said physical structure component comprising at least first and second biological tissue sheet members, said first and second biological tissue sheet members comprising a biological tissue multi-sheet structure, said multi-sheet structure comprising an internal lumen adapted to transmit fluid flow therethrough, a proximal valve annulus engagement end and a distal end, said proximal valve annulus engagement end being configured to engage said AV valve annulus region, said proximal valve annulus engagement end of said multi-sheet structure comprising a circumferential ribbon connection region and a plurality of equally spaced ribbons projecting from said circumferential ribbon connection region toward said multi-sheet structure distal end, each of said plurality of ribbons comprising proximal and distal ends, a first edge region extending from said proximal end of each of said plurality of ribbons to said distal end of each of said plurality of ribbons and a second edge region extending from said proximal end of each of said plurality of ribbons to said distal end of each of said plurality of ribbons, said proximal end of each of said plurality of ribbons being connected to said circumferential ribbon connection region, said plurality of ribbons being positioned circumferentially about said circumferential ribbon connection region, wherein said first edge regions of said plurality of ribbons are positioned proximate said second edge regions of said plurality of ribbons, wherein a plurality of fluid flow modulating regions is formed between adjacent ribbons of said plurality of ribbons, said distal ends of said plurality of ribbons being disposed proximate each other in a joined relationship, wherein said fluid flow through said distal end of said multi-sheet structure is restricted while said fluid flow is allowed to be transmitted through said fluid flow modulating regions when in an open position, said multi-sheet structure being configured to transition from an expanded position when said proximal valve annulus engagement end of said multi-sheet structure is engaged to said AV valve annulus region, receives said fluid flow therein, and said fluid flow exhibits a first fluid pressure of said plurality of fluid pressures, to a collapsed position when said fluid flow exhibits a second fluid pressure of said plurality of fluid pressures, said plurality of fluid flow modulating regions being configured to transition from said open position when said multi-sheet structure is in said expanded position, wherein said plurality of fluid flow modulating regions allow said fluid flow to be transmitted through said multi-sheet structure, to a closed position when said multi-sheet structure is in said collapsed position, wherein said plurality of fluid flow modulating regions restrict said fluid flow through said multi-sheet structure, said support structure comprising an annular ring and a plurality of elongated cardiovascular structure engagement members, each of said plurality of elongated cardiovascular structure engagement members comprising proximal and distal ends, said annular ring being adapted to transition from a contracted pre-deployment configuration, wherein said annular ring is positioned in said multi-sheet structure lumen, to an expanded post-deployment configuration, whereby, said annular ring is positioned in said multi-sheet structure lumen proximate said proximal valve annulus engagement end, said multi-sheet structure is positioned in said expanded position, wherein said proximal valve annulus engagement end is disposed proximate said plurality of elongated cardiovascular structure engagement members, said annular ring comprising a first edge region and a second edge region, said proximal ends of said plurality of elongated cardiovascular structure engagement members being connected to said annular ring first edge region and projecting longitudinally therefrom, said distal ends of said plurality of elongated cardiovascular structure engagement members comprising tissue engaging means adapted to engage a cardiovascular structure, said support structure being disposed in line with said proximal valve annulus engagement end between said first and second sheet members of said multi-sheet structure, whereby each of said plurality elongated cardiovascular structure engagement members extends through and out of said distal end of said multi-sheet structure.

2. The prosthetic valve of claim 1, wherein said mammalian tissue source is selected from the group consisting of the heart, small intestine, large intestine, stomach, lung, liver, kidney, pancreas, peritoneum, placenta, amniotic membrane, umbilical cord, bladder, prostate, and any fetal tissue from any mammalian organ.

3. The prosthetic valve of claim 2, wherein said mammalian-based tissue comprises an ECM composition comprising acellular ECM derived from said mammalian tissue source.

4. The prosthetic valve of claim 1, wherein said mammalian-based tissue comprises collagenous mammalian tissue.

5. The prosthetic valve of claim 4, wherein said collagenous mammalian tissue comprises pericardium tissue.

6. The prosthetic valve of claim 1, wherein said mammalian-based tissue further comprises at least one exogenously added biologically active agent.

7. The prosthetic valve of claim 6, wherein said biologically active agent comprises a cell selected from the group consisting of a human embryonic stem cell, fetal cardiomyocyte, myofibroblast, and mesenchymal stem cell.

8. The prosthetic valve of claim 6, wherein said biologically active agent comprises a growth factor selected from the group consisting of a transforming growth factor-alpha (TGF-α), transforming growth factor-beta (TGF-β), fibroblast growth factor-2 (FGF-2), and vascular endothelial growth factor (VEGF).

9. The prosthetic valve of claim 6, wherein said pharmacological agent comprises an agent selected from the group consisting of an antibiotic, anti-viral agent, analgesic, anti-inflammatory, anti-neoplastic, anti-spasmodic, anti-coagulant and anti-thrombotic.

10. The prosthetic valve of claim 1, wherein said mammalian-based tissue further comprises a pharmacological agent.

11. The prosthetic valve of claim 1, wherein said support structure annular ring comprises a first biocompatible metal selected from the group consisting of a shape memory nickel-titanium alloy, titanium, stainless steel and magnesium.

12. The prosthetic valve of claim 1, wherein said support structure annular ring comprises a first polymeric composition comprising a first biocompatible polymer selected from the group consisting of polyurethane urea (Artelon®), poly(ε-caprolactone) (PCL), poly(glycerol sebacate) (PGS) and poly(glycerol sebacate) acrylate (PGSA).

13. The prosthetic valve of claim 1, wherein said support structure annular ring comprises a first outer coating.

14. The prosthetic valve of claim 13, wherein said first outer coating comprises an immunomodulating compound.

15. The prosthetic valve of claim 13, wherein said first coating comprises a fibrin-based adhesive composition.

16. The prosthetic valve of claim 13, wherein said first outer coating comprises a collagen-based adhesive composition.

17. The prosthetic valve of claim 13, wherein said first outer coating comprises an anti-proliferative agent.

18. The prosthetic valve of claim 1, wherein said plurality of cardiovascular structure engagement members comprises a second biocompatible metal selected from the group consisting of a shape memory nickel-titanium alloy, titanium, stainless steel and magnesium.

19. The prosthetic valve of claim 1, wherein said plurality of cardiovascular structure engagement members comprises a second polymeric composition comprising a second biocompatible polymer selected from the group consisting of polyurethane urea (Artelon®), poly(ε-caprolactone) (PCL), poly(glycerol sebacate) (PGS) and poly(glycerol sebacate) acrylate (PGSA).

20. The prosthetic valve of claim 1, wherein each of said plurality of cardiovascular structure engagement members comprises a high molecular weight polyethylene (HMPE) fiber.

21. The prosthetic valve of claim 20, wherein said HMPE fiber comprises Dyneema®.

22. The prosthetic valve of claim 1, wherein each of said plurality of cardiovascular structure engagement members comprises a second outer coating.

23. The prosthetic valve of claim 22, wherein said second outer coating comprises an anti-proliferative agent.

* * * * *